United States Patent
Hwu et al.

(10) Patent No.: US 10,894,044 B2
(45) Date of Patent: Jan. 19, 2021

(54) COMBINATION OF TOPOISOMERASE-I INHIBITORS WITH IMMUNOTHERAPY IN THE TREATMENT OF CANCER

(71) Applicant: Board of Regents, The University of Texas System, Austin, TX (US)

(72) Inventors: Patrick Hwu, Houston, TX (US); Jodi A. McKenzie, Houston, TX (US); Rina M. Mbofung, Houston, TX (US); Rodabe Amaria, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 223 days.

(21) Appl. No.: 15/760,995

(22) PCT Filed: Sep. 16, 2016

(86) PCT No.: PCT/US2016/052303
§ 371 (c)(1),
(2) Date: Mar. 16, 2018

(87) PCT Pub. No.: WO2017/049199
PCT Pub. Date: Mar. 23, 2017

(65) Prior Publication Data
US 2018/0263971 A1   Sep. 20, 2018

Related U.S. Application Data

(60) Provisional application No. 62/219,548, filed on Sep. 16, 2015.

(51) Int. Cl.
| | |
|---|---|
| *A61K 31/4745* | (2006.01) |
| *A61K 9/00* | (2006.01) |
| *A61K 39/395* | (2006.01) |
| *C07K 16/28* | (2006.01) |
| *A61K 9/127* | (2006.01) |
| *A61P 35/00* | (2006.01) |
| *A61K 39/00* | (2006.01) |

(52) U.S. Cl.
CPC ........ *A61K 31/4745* (2013.01); *A61K 9/0019* (2013.01); *A61K 9/127* (2013.01); *A61K 9/1271* (2013.01); *A61K 39/3955* (2013.01); *A61P 35/00* (2018.01); *C07K 16/2818* (2013.01); *C07K 16/2827* (2013.01); *C07K 16/2878* (2013.01); *A61K 2039/505* (2013.01); *A61K 2039/507* (2013.01); *A61K 2039/545* (2013.01); *A61K 2300/00* (2013.01); *C07K 2317/76* (2013.01)

(58) Field of Classification Search
None
See application file for complete search history.

(56) References Cited

U.S. PATENT DOCUMENTS

| | | |
|---|---|---|
| 2006/0165744 A1 | 7/2006 | Jamil |
| 2015/0182521 A1 | 7/2015 | Bayever |
| 2015/0202291 A1 | 7/2015 | Bosch |
| 2019/0167661 A1* | 6/2019 | Adiwijaya ............. A61P 35/00 |

FOREIGN PATENT DOCUMENTS

| | | |
|---|---|---|
| WO | 2013173223 | 11/2013 |
| WO | 2013188586 | 12/2013 |
| WO | 2015016718 | 2/2015 |
| WO | 2015095423 | 6/2015 |
| WO | 2015134605 | 9/2015 |
| WO | 2016040880 | 3/2016 |
| WO | 2017049199 A1 | 3/2017 |

OTHER PUBLICATIONS

Anonymous, "Study of Pembrolizumab Plus Chemotherapy in Patients with Advanced Cancer (PembroPlus)", ClinicalTrials.gov, Jan. 5, 2015, Retrieved from the Internet: URL:https://clinicaltrials.gov/archive/NCT02331251/2015_01_05.
Hoskins, J. et al., "UGT1A1*28 Genotype and Irinotecan-Induced Neutropenia: Dose Matters", J Natl Cancer Inst., 99(17):1290-5, (2007).
Larkin, J. et al., "Combined Nivolumab and Ipilimumab or Monotherapy in Untreated Melanoma", N Engl J Med., 373(1):23-34, (2015).
Clinicaltrials.gov, NCT02331251 on Jan. 5, 2015; https://clinicaltrials.gov/archive/NCT0233125/2015_01_05, p. 1-3; p. 1.
Clinicaltrials.gov, NCT02423954 on Apr. 21, 2015; https://clinicaltrials.gov/archive/NCT02423954/2015_04_21, p. 1-2; p. 1.
Drummond, D. et al., "Development of a highly active nanoliposomal irinotecan using a novel intraliposomal stabilization strategy", Cancer Res, 66(6):3271-7, (2015).
International Application No. PCT/US2016/052303; International Preliminary Report on Patentability, dated Mar. 20, 2018; 6 pages.
International Application No. PCT/US2016/52303; International Search Report and Written Opinion of the International Searh Authority, dated Dec. 9, 2016; 9 pages.
Larkin, et al, "Combined Nivolumab and Ipilimumab or Monotherapy in Untreated Melanoma", The New England Journal of Medicine, May 31, 2015, vol. 373, p. 23-34; p. 23, para 1; p. 24, para 4.
McKenzie, J. et al., "Increasing the antitumor efficacy of immunotherapy in melanoma by using topoisomerase I inhibitors [abstract], Proceedings of the CRI-CIMT-EATI-AACR Inaugural International Cancer Immunotherapy Conference: Translating Science into Survival", AACR Cancer Immunol Res, 4(1 Suppl):Abstract No. B152, (2015).

(Continued)

*Primary Examiner* — Peter J Reddig
(74) *Attorney, Agent, or Firm* — Dennis A. Bennett; Cynthia Hathaway; John Deeper

(57) ABSTRACT

The present disclosure relates to compositions and methods for treating cancer, more specifically to methods and compositions comprising a Topoisomerase I inhibitor and an α-PD-L1 antibody.

12 Claims, 26 Drawing Sheets

(56) References Cited

OTHER PUBLICATIONS

Package Insert, Onivyde® (irinotecan liposomal injection), Merrimack Pharmaceuticals, Inc., first approved 1996.
Package Insert, Opdivo® (nivolumab), Bristol Myers Squibb Co., first approved 2014, revised Mar. 2015.
Package Insert, Yervoy (ipilimumab), Bristol Myers Squibb Co., first approved 2011, revised Dec. 2013.
Silva, "NivoPlus Clinical Trial Currently Recruiting Patients With Advanced Cancer" Immunooncology News, Jun. 29, 2015, p. 1-4, p. 1, para 1; p. 2, para 2-3.
U.S. Appl. No. 15/760,995; Application as filed dated Mar. 16, 2018; 49 pages.
Chang, T. et al., "Phase I Study of Nanoliposomal Irinotecan (PEP02) in Advanced Solid Tumor Patients", Cancer Chemother Pharmacol., 75(3):579-86, (2015).
Kalra, A. et al., "Preclinical Activity of Nanoliposomal Irinotecan is Governed by Tumor Deposition and Intratumor Prodrug Conversion", Cancer Res., 74(23):7003-13, (2014).

\* cited by examiner

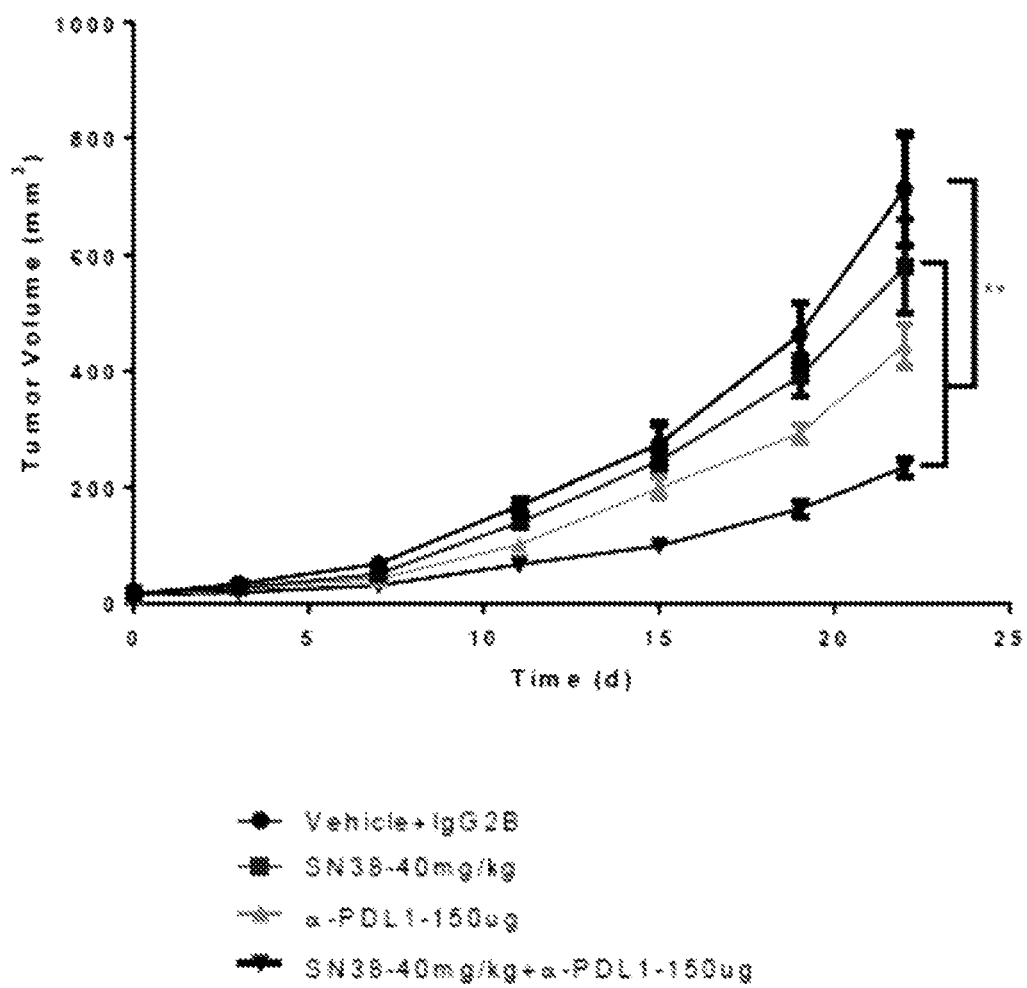

FIG. 6
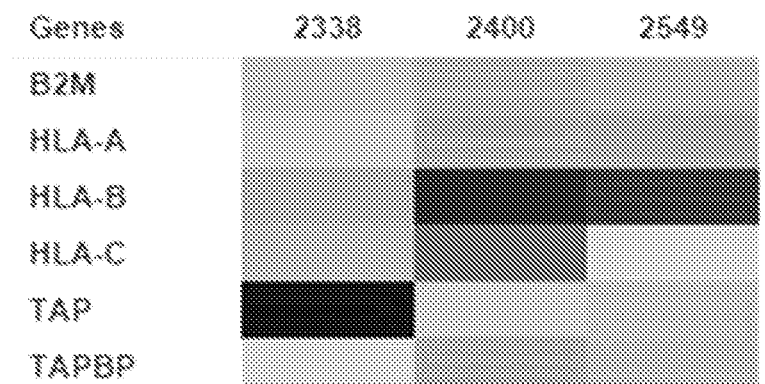
FIG. 6A
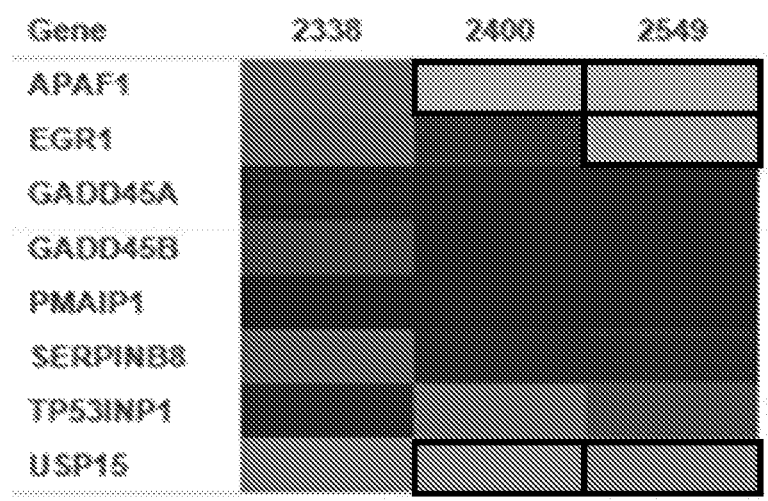
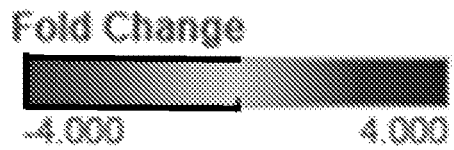
FIG. 6B $$COMBOSCORE = [\frac{(\%Caspase + Tumor\ cells)_{Drug + Tcells} - (\%Caspase + Tumor\ cells)_{Drug}}{(\%Caspase + Tumor\ cells)_{Control + Tcells} - (\%Caspase + Tumor\ cells)_{Control}}]^2$$

Resistance to T-cell Mediated killing

Enhanced T-cell Mediated killing

COMBINATION OF TOPOISOMERASE-I INHIBITORS WITH IMMUNOTHERAPY IN THE TREATMENT OF CANCER

This application claims the benefit of priority of U.S. provisional application No. 62/219,548, filed Sep. 16, 2015, the disclosure of which is hereby incorporated by reference as if written herein in its entirety.

TECHNICAL FIELD

The present disclosure relates to compositions and methods for treating cancer, more specifically to methods and compositions comprising a Topoisomerase I inhibitor and an α-PD-L1 or α-PD-1 antibody.

BACKGROUND

Generally, cancer results from the deregulation of the normal processes that control cell division, differentiation, and apoptotic cell death and is characterized by the proliferation of malignant cells which have the potential for unlimited growth, local expansion and systemic metastasis. Deregulation of normal processes include abnormalities in signal transduction pathways and response to factors which differ from those found in normal cells.

Topoisomerases are a family of DNA enzymes, which are involved in unwinding DNA and relieving torsional strain during replication and transcription. Topoisomerases are nuclear enzymes that control the changes in DNA structure by catalyzing the breaking and rejoining of the phosphodiester backbone of DNA strands during the normal cell cycle. These enzymes allow DNA to relax by forming enzyme-bridged strand breaks that act as transient gates or pivotal points for the passage of other DNA strands. Topoisomerase-inhibiting drugs appear to interfere with this breakage-reunion reaction of DNA topoisomerases, which ultimately leads to cell death. Topoisomerase-inhibiting drugs have been found to be effective for inhibiting cancer cell proliferation.

In addition to preventing proliferation of tumor cells themselves, stimulating the patient's own immune response to target tumor cells is another option for cancer therapy and many studies have demonstrated effectiveness of immunotherapy using tumor antigens to induce the immune response. PD-L1 (Programmed Cell Death Ligand-1) binds PD-1 (Programmed Cell Death Protein 1) and thus both play a role in the regulation of the immune system functions including immunity and self-tolerance. PD-L1 is expressed in tumors, and it appears that upregulation of PD-L1 may allow cancers to evade the host immune system. Thus, interfering with the inhibitory signal through the PD-L1:PD-1 pathway is a therapeutic option for enhancing anti-tumor immunity. Antibodies blocking activation of the programmed cell death 1 (PD-1) receptor have been found to be effective for strengthening immune cells to target cancer cells, however, long lasting responses are only observed in a small subset of immunotherapy-treated patients.

Melanoma is a highly aggressive form of skin cancer, whose rates of morbidity and mortality are continuously increasing. The development of immunotherapeutic agents like anti-PD-L1 and anti-CTLA4 antibodies has resulted in fundamental advances in the treatment of melanoma. However, long lasting responses are only observed in a small subset of immunotherapy-treated melanoma patients. This shortfall highlights the need for a better understanding of the molecular mechanisms that govern tumor sensitivity or resistance to immunotherapy.

Despite these advances, there remains a need for improved methods and compositions for treating cancer. This disclosure relates to combining therapeutic approaches for inhibiting proliferation of tumor cells and enhancing anti-tumor immunity. For example, observed clinical responses to oncology immune-therapy have been heterogeneous and limited in some patients due to a variety of factors including, for example, patients having immune sterile tumors, higher mutational loads, intra- and inter-tumoral variabilities due to genetic and epigenetic differences between patient cancers, and other still unknown mechanisms believed to mediate responses or resistance to immune-therapy in the field of oncology. As a result, immune-therapy has had limited clinical benefit in some patients due to an inability to accurately predict response to immuno-therapy. There remains a need to make tumors more immunogenic and increase the efficacy of immune-therapy in oncology treatment.

SUMMARY

In some embodiments, inventors have discovered that treating tumor cells with certain bioactive compounds may enhance the sensitivity of the patient-derived tumor cells to T-cell mediated cytotoxicity, thereby providing novel combinatorial drug therapies to improve the efficacy of cancer immunotherapy. For example, the inventors herein disclose a synergistic effect between Top1 inhibitors and immune-based therapies in the treatment of cancer. The invention is based in part on the discovery that treatment of melanoma tumor cells with a Top1 inhibitor prior to exposure to autologous T cells, produced a synergistic increase in tumor cell death, as measured by intracellular staining of activated caspase 3, and computed using CalcuSyn.

In one embodiment, a screening approach is disclosed for assaying T-cell mediated cytotoxicity. In another embodiment, certain topoisomerase I inhibitors are identified as enhancers of T cell mediated immune-therapy, including therapeutic combinations that can provide a synergistic improvement of CTL-mediated killing in vitro and enhanced anti-tumor response using a combination of liposomal irinotecan (e.g., MM-398) and anti-PD-L1 or anti-PD-1 antibody in vivo. In another embodiment, the role of a p53 regulatory gene is identified as playing an essential role in the enhanced response to T cell mediated killing, including topoisomerase I inhibition resulting in upregulation of Teap, Teap overexpression observed to recapitulate the relevant phenotype and the observation that knockdown of Teap impedes the relevant phenotype.

Autologous patient-derived tumor cell lines and tumor infiltrating lymphocytes (TILs) were utilized in an in vitro activated caspase 3-based high-throughput screen, to identify compounds that increase the sensitivity of melanoma cells to T-cell mediated cytotoxicity. The screen consisted of a library of 850 bioactive compounds. One group of compounds that was most able to enhance T-cell killing of melanoma cells was topoisomerase I (Top1) inhibitors including: topotecan, and irinotecan. Also disclosed herein is an in vivo model, where a better anti-tumor effect was observed in tumor-bearing mice treated with an antibody against the co-inhibitory molecule Programmed Death Ligand 1 (PD-L1) in combination with a nanoparticle liposomal formulation of irinotecan, than in cohorts treated with either antibody or drug alone. These findings relate to synergism between Top1 inhibitors and immune-based therapies in the treatment of melanoma.

Genomic and proteomic changes elicited by inhibition of Top1 are now being investigated to identify the molecular factors that mediate the effect of Top1 inhibitors on T cell-mediated killing of melanoma. Our goal is to identify molecular changes mediated by Top1 inhibition in melanoma tumor cells, and/or the tumor microenvironment, can relieves immunosuppression and potentiates the activity of cytotoxic T cell-based immunotherapy.

Provided is a method for killing cancer cells in a biological sample comprising contacting the biological sample with an effective amount of a Topoisomerase I inhibitor and an α-PD-L1 antibody.

Provided is a method for inhibiting the growth of cancer cells in a biological sample comprising contacting the biological sample with an effective amount of a Topoisomerase I inhibitor and an α-PD-L1 antibody.

Provided is a method for treating a cancer in a subject in need thereof, comprising the step of administering to the subject an effective amount of a Topoisomerase I inhibitor and an α-PD-L1 antibody.

Provided is a method of treating cancer comprising the administration of a therapeutically effective amount of an α-PDL-1 antibody and a topoisomerase I inhibitor. In one aspect, methods of treating cancer can include administering to a patient in need thereof a therapeutically effective amount of the α-PDL-1 antibody followed by the topoisomerase I inhibitor. In another aspect, the topoisomerase I inhibitor is a liposomal irinotecan formulation such as MM-398.

Provided is a composition comprising an effective amount of a Topoisomerase I inhibitor and an α-PD-L1 antibody.

Provided is a composition comprising an effective amount of a Topoisomerase I inhibitor and an α-PD-L1 antibody for use in treating cancer.

Provided is a use of a composition as recited in claim 23 for the manufacture of a medicament to treat cancer.

Provided is a kit for treating a cancer in a subject in need thereof, comprising: a) a Topoisomerase I inhibitor and an α-PD-L1 antibody; and b) written instructions for administering to the subject an effective amount of a Topoisomerase I inhibitor and an α-PD-L1 antibody to treat the cancer.

Provided is a method for killing cancer cells in a biological sample comprising contacting the biological sample with an effective amount of a Topoisomerase I inhibitor and an α-PD-1 antibody.

Provided is a method for inhibiting the growth of cancer cells in a biological sample comprising contacting the biological sample with an effective amount of a Topoisomerase I inhibitor and an α-PD-1 antibody.

Provided is a method for treating a cancer in a subject in need thereof, comprising the step of administering to the subject an effective amount of a Topoisomerase I inhibitor and an α-PD-1 antibody.

Provided is a method of treating cancer comprising the administration of a therapeutically effective amount of an α-PD-1 antibody and a topoisomerase I inhibitor. In one aspect, methods of treating cancer can include administering to a patient in need thereof a therapeutically effective amount of the α-PD-1 antibody followed by the topoisomerase I inhibitor. In another aspect, the topoisomerase I inhibitor is a liposomal irinotecan formulation such as MM-398.

Provided is a composition comprising an effective amount of a Topoisomerase I inhibitor and an α-PD-1 antibody.

Provided is a composition comprising an effective amount of a Topoisomerase I inhibitor and an α-PD-1 antibody for use in treating cancer.

Provided is a use of a composition as recited in claim 23 for the manufacture of a medicament to treat cancer.

Provided is a kit for treating a cancer in a subject in need thereof, comprising: a) a Topoisomerase I inhibitor and an α-PD-1 antibody; and b) written instructions for administering to the subject an effective amount of a Topoisomerase I inhibitor and an α-PD-1 antibody to treat the cancer.

BRIEF DESCRIPTION OF THE DRAWINGS

FIG. 3 depicts the combination Index of the Top1 inhibitor SN38 and T cell cytotoxicity.

FIG. 4 depicts the results of two in vivo experiments in C57BL/6 mice inoculated sc with $5\times10^5$ MC38/gp100 cells and then treated with vehicle, SN38, α-PD-L1, or a combination of SN38 and α-PD-L1 (FIG. 4A), or free irinotecan or MM-398 (FIG. 4B). FIG. 4C depicts the results of an in vivo experiments in C57BL/6 mice inoculated sc with $5\times10^5$ MC38/gp100 cells and then treated with vehicle, SN38, α-PD-L1, or a combination of SN38 and α-PD-L1. This is a repeat of the experiment represented in FIG. 4A with the notable change that treatment began 3 days after tumor inoculation (FIG. 4C) as opposed to 7 days after tumor inoculation (FIG. 4A). The data represented in FIG. 4C were pulled from the experiment described on FIG. 10. This shows the enhanced tumor control observed in tumor-bearing mice treated with a combination of SN38 and anti-PD-L1 in comparison to the control group or to cohorts treated with SN38 or anti-PD-L1 alone.

FIG. 6 shows gene expression changes in antigen processing genes after Top1 inhibition. The heatmap in FIG. 6A represents the differential expression of a subset of genes involved in antigen presentation. The heatmap in FIG. 6B represents a subset of genes differentially expressed after Top1 inhibition from microarray analysis. In FIG. 6B, the leftmost side of the fold-change spectrum, indicating down-regulation, has been outlined to distinguish it from upregulation, and the genes that were downregulated in the array (APAF1 and USP15 in 2400 and 2549, and EGR1 in 2549) have been outlined as well.

DETAILED DESCRIPTION

Abbreviations and Definitions

Figure 1A:
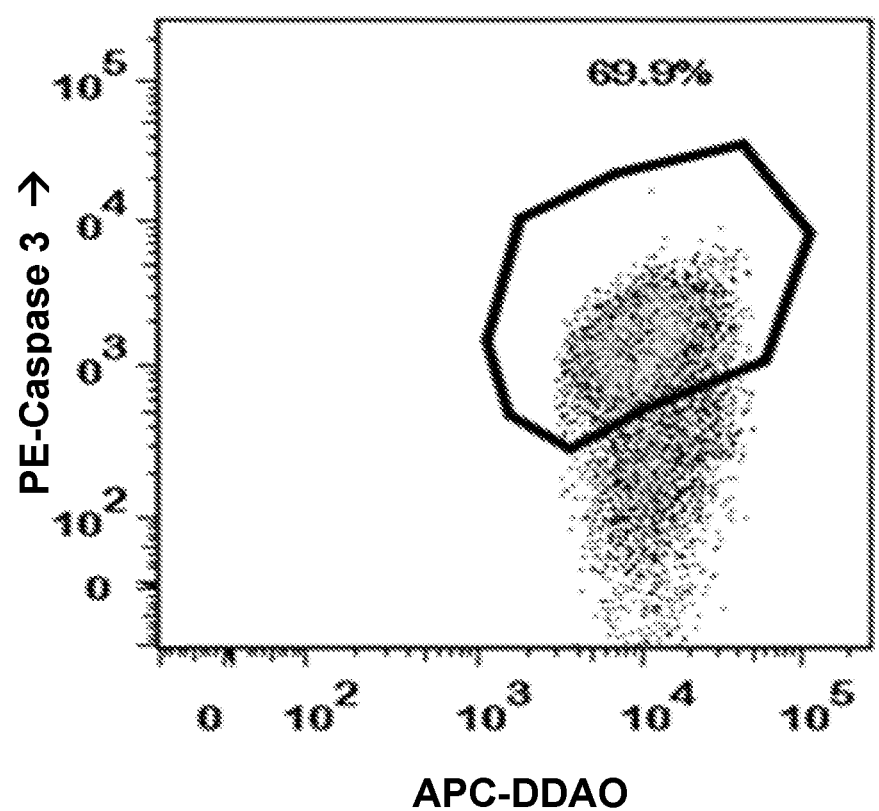
FIG. 1 depicts the FACS analysis (1A) to determine tumor cells, stained with the cell tracker dye DDAO, which are also positive for activated caspase 3 and a schematic (1B) for obtaining data.

To facilitate understanding of the disclosure, a number of terms and abbreviations as used herein are defined below as follows:

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

The term "about," as used herein when referring to a measurable value such as an amount of a compound, dose, time, temperature, and the like, is meant to encompass variations of 20%, 10%, 5%, 1%, 0.5%, or even 0.1% of the specified amount.

Camptothecin is a drug used for the treatment of cancer, and inhibits the DNA enzyme topoisomerase I. Its IUPAC name is (S)-4-ethyl-4-hydroxy-1H-pyrano[3',4':6,7]indolizino[1,2-b] quinoline-3,14-(4H,12H)-dione.

The term "effective amount" as used herein means that the amount of a Topoisomerase I inhibitor and an α-PD-L1 antibody contained in the composition administered is of sufficient quantity to achieve the intended purpose, such as, in this case, to kill cancer cells in a biological sample, inhibit the growth of cancer cells in a biological sample, or treat a cancer in a subject in need thereof.

The term "humanized monoclonal antibodies" means that at least a portion of the exposed amino acids in the framework regions of the antibody (or fragment), which do not match with the corresponding amino acids in the most homologous human counterparts, are changed, such as by site directed mutagenesis of the DNA encoding the antibody. The term "humanized monoclonal antibody" also includes chimeric antibody wherein the light and heavy variable regions of a monoclonal antibody generated by a hybridoma from a non-human call line are each attached, via recombinant technology, to one human light chain constant region and at least one heavy chain constant region, respectively.

Irinotecan is a drug used for the treatment of cancer, and inhibits the DNA enzyme topoisomerase I. Its IUPAC name is (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate.

Lamellarin D is a drug used for the treatment of cancer, and inhibits the DNA enzyme topoisomerase I. Its IUPAC name is 3,11-Dihydroxy-14-(4-hydroxy-3-methoxyphenyl)-2,12-dimethoxy-6H-chromeno[4',3':4,5]pyrrolo[2,1-a]isoquinolin-6-one.

MM-398 is nano-liposomal irinotecan (nal-IRI), a liposomal encapsulation of irinotecan (~80,000 molecules/liposome) that is engineered for stable encapsulation and prolonged circulation. The $AUC_{0-t}$ of total irinotecan delivered by MM-398 in blood is 1,652 hr·µg/mL (120 mg/m$^2$) and the $AUC_{0-t}$ of the active metabolite, SN-38, is 476 hr·ng/mL.

The $T_{1/2}$ of total irinotecan in blood is 21.2 h and of SN-38, 88.8 h. MM-398 is sold under the trade name ONIVYDE® (irinotecan liposome injection) (Merrimack Pharmaceuticals, Cambridge, Mass.).

Nivolumab is a human IgG4 anti-PD-1 monoclonal antibody against the programmed cell death receptor 1, and used in the treatment of cancer.

Pembrolizumab is a human IgG4 anti-PD-1 monoclonal antibody against the programmed cell death receptor 1, and used in the treatment of cancer.

SN-38 is the active metabolite of irinotecan; it is 1000 times more active than irinotecan itself. In vitro cytotoxicity assays show that the potency of SN-38 relative to irinotecan varies from 2- to 2000-fold. Its IUPAC name is (4S)-4,11-Diethyl-4,9-dihydroxy-1H-pyrano[3',4':6,7]indolizino[1,2-b]quinoline-3,14(4H,12H)-dione.

Anti-PD-L1 antibodies are known in the art and include the mouse PD-L1-PE (clone 10F.9G2) which may be readily obtained from a number of sources (e.g., Bio X Cell, 10 Technology Dr., Suite 2B, West Lebanon, N.H. 03784-1671 USA). See also, Rodig N et al., "Endothelial expression of PD-L1 and PD-L2 down-regulates CD8+ T cell activation and cytolysis," Eur J Immunol 2003; 33:3117-3126; Brown J A et al., "Blockade of programmed death-1 ligands on dendritic cells enhances T cell activation and cytokine production," J Immunol. 2003 Feb. 1; 170(3):1257-66; and Drees J J et al., "Soluble production of a biologically active single-chain antibody against murine PD-L1 in *Escherichia coli*," Protein Expr Purif, 2014 Febuary; 94:60-6. Avelumab, atezolizumab, and durvalumab are anti-PD-L1 antibodies under development.

Anti-PD-1 antibodies are known in the art and include nivolumab and pembrolizumab.

The term topoisomerase I inhibitor refers to agents designed to interfere with the action of topoisomerase enzyme I which controls the changes in DNA structure by catalyzing the breaking and rejoining of the phosphodiester backbone of DNA strands during the normal cell cycle.

The term synergy refers to a phenomenon where treatment with a combination of therapeutic agents manifests a therapeutically superior outcome to the outcome achieved by each individual constituent of the combination used at its optimum dose (T. H. Corbett et al., 1982, Cancer Treatment Reports, 66, 1187). In this context a therapeutically superior outcome is one in which the patients either a) exhibit fewer incidences of adverse events while receiving a therapeutic benefit that is equal to or greater than that where individual constituents of the combination are each administered as monotherapy at the same dose as in the combination, or b) do not exhibit dose-limiting toxicities while receiving a therapeutic benefit that is greater than that of treatment with each individual constituent of the combination when each constituent is administered in at the same doses in the combination(s) as is administered as individual components. In xenograft models, a combination, used at its maximum tolerated dose, in which each of the constituents will be present at a dose generally not exceeding its individual maximum tolerated dose, manifests therapeutic synergy when decrease in tumor growth achieved by administration of the combination is greater than the value of the decrease in tumor growth of the best constituent when the constituent is administered alone.

Thus, in combination, the components of such combinations have an additive or superadditive effect on suppressing pancreatic tumor growth, as compared to monotherapy. By "additive" is meant a result that is greater in extent (e.g., in the degree of reduction of tumor mitotic index or of tumor growth or in the degree of tumor shrinkage or the frequency and/or duration of symptom-free or symptom-reduced periods) than the best separate result achieved by monotherapy with each individual component, while "superadditive" is used to indicate a result that exceeds in extent the sum of such separate results.

Topotecan is a drug used for the treatment of cancer, and inhibits the DNA enzyme topoisomerase I. Its IUPAC name is (S)-10-[(dimethylamino)methyl]-4-ethyl-4,9-dihydroxy-1H-pyrano[3',4':6,7]indolizino[1,2-b] quinoline-3,14(4H,12H)-dione monohydrochloride.

An α-PD-L1 antibody is a monoclonal antibody that works to activate the immune system by targeting Programmed cell death ligand 1. An α-PD-1 antibody is a monoclonal antibody that works to activate the immune system by targeting Programmed cell death protein 1. Since PD-1 is the receptor for PD-L1, interference with (e.g. inhibition of) either of these targets (inhibition of the interaction between them) permits improved immunologic targeting of cancer cells via immune checkpoint blockade.

The term "subject" includes all mammals including humans, and is equivalent to the terms "patient" and "host." Examples of subjects include humans, cows, dogs, cats, goats, sheep, pigs, and rabbits. Preferably, the subject is a human.

Methods

Provided is a method for killing cancer cells in a biological sample comprising contacting the biological sample with an effective amount of a Topoisomerase I inhibitor and an α-PD-L1 or α-PD-1 antibody.

Provided is a method for inhibiting the growth of cancer cells in a biological sample comprising contacting the biological sample with an effective amount of a Topoisomerase I inhibitor and an α-PD-L1 or α-PD-1 antibody.

Provided is a method for treating a cancer in a subject in need thereof, comprising the step of administering to the subject an effective amount of a Topoisomerase I inhibitor and an α-PD-L1 or α-PD-1 antibody. In certain embodiments, the α-PD-L1 or α-PD-1 antibody is a humanized monoclonal antibody.

In certain embodiments, the subject is a human.

In certain embodiments, the cancer is chosen from skin cancer, or a variant thereof.

In certain embodiments, administration of the Topoisomerase I inhibitor and α-PD-L1 antibody is sequential.

In certain embodiments, administration of the Topoisomerase I inhibitor occurs before administration of the α-PD-L1 antibody.

In certain embodiments, administration of the α-PD-L1 or α-PD-1 antibody occurs before administration of the Topoisomerase I inhibitor.

In certain embodiments, administration of the α-PD-L1 or α-PD-1 antibody and Topoisomerase I inhibitor is essentially simultaneous.

In certain embodiments, the α-PD-1 antibody is chosen from nivolumab and pembrolizumab.

In certain embodiments, the Topoisomerase I inhibitor is chosen from irinotecan, topotecan, camptothecin and lamellarin D. In some embodiments, the method as recited in claim 12, wherein the Topoisomerase I inhibitor is irinotecan. In some embodiments, the irinotecan is provided in a composition comprising liposomes (liposomal irinotecan).

In particular embodiments, the irinotecan is provided in a composition comprising liposomes in an aqueous medium, the liposomes having an interior aqueous space separated from the aqueous medium by a membrane, the membrane comprising lipids, the lipids comprising an uncharged lipid component and a neutral phospholipid, with, entrapped inside the liposomes:

a. irinotecan and sucrose octasulfate, or b. irinotecan and sucrose octasulfate and a substituted ammonium compound, wherein, when administered into the bloodstream of a mammal, said irinotecan has a half-release time from said liposomes of at least 24 hours and the irinotecan entrapped inside the liposomes is at a concentration that exceeds the irinotecan concentration in the aqueous medium.

In particular embodiments, the liposomal irinotecan is nano-liposomal irinotecan. In particular embodiments, the liposomal irinotecan is MM-398 (ONIVYDE®).

In particular embodiments, the method comprises at least one cycle, wherein the liposomal irinotecan is administered on day 1 of a cycle at a dose of between about 60 and about 180 mg/m$^2$, except if the patient is homozygous for the UGT1A1*28 allele, wherein the liposomal irinotecan is administered on day 1 of cycle 1 at a dose of between about 40 and about 120 mg/m$^2$, wherein the cycle is a period of 2 to 3 weeks. In particular embodiments, the liposomal irinotecan is administered on day 1 of a cycle at a dose of between about 90 and about 150 mg/m$^2$, except if the patient is homozygous for the UGT1A1*28 allele, wherein the liposomal irinotecan is administered on day 1 of cycle 1 at a dose of between about 60 and about 100 mg/m$^2$. In particular embodiments, the method comprises at least one cycle, wherein the liposomal irinotecan is administered on day 1 of a cycle at a dose of 120 mg/m$^2$, except if the patient is homozygous for the UGT1A1*28 allele, wherein the liposomal irinotecan is administered on day 1 of cycle 1 at a dose of 80 mg/m$^2$. In particular embodiments, the cycle is a period of 2 weeks. In particular embodiments, the cycle is a period of 3 weeks.

Also provided herein is a method of treatment of cancer in a host in need thereof, comprising the step of administering to the host an effective amount of a Topoisomerase I inhibitor and either an α-PD-1 or α-PD-L1 antibody. In certain embodiments, the Topoisomerase I inhibitor and either α-PD-1 or α-PD-L1 antibody are each administered in an amount and in a schedule of administration that is therapeutically synergistic in the treatment of said cancer. In certain embodiments, the method comprises the step of administering to the host an effective amount of a Topoisomerase I inhibitor and an α-PD-1 antibody. In certain embodiments, the method comprises the step of administering to the host an effective amount of a Topoisomerase I inhibitor and an α-PD-L1 antibody.

In certain embodiments, the Topoisomerase I inhibitor is irinotecan. In certain embodiments, the Topoisomerase I inhibitor is liposomal irinotecan. In certain embodiments, the Topoisomerase I inhibitor is MM-398.

In certain embodiments, the Topoisomerase I inhibitor and either α-PD-1 or α-PD-L1 antibody are administered every two to three weeks.

In certain embodiments, the α-PD-1 antibody is chosen from nivolumab and pembrolizumab.

In certain embodiments, provided herein is are methods of treatment of cancer in a host in need thereof comprising the administration of a combination of liposomal irinotecan and nivolumab, in an amount and in a schedule of administration that is therapeutically synergistic in the treatment of said cancer.

In certain embodiments, said schedule comprises administering to a human host during a 28-day treatment cycle: a total of 50 mg/m$^2$ liposomal irinotecan (free base) followed by the administration of 3 mg/kg nivolumab, once every two weeks for two weeks; and repeating said 28-day treatment cycle until a progression or an unacceptable toxicity is observed.

In certain embodiments, said schedule comprises administering to a human host during a 28-day treatment cycle: a total of 43 mg/m$^2$ liposomal irinotecan (free base) followed by the administration of 3 mg/kg nivolumab, once every two weeks for two weeks; and repeating said 28-day treatment cycle until a progression or an unacceptable toxicity is observed.

In certain embodiments, said schedule comprises administering to a human host during a 28-day treatment cycle: a total of 70 mg/m$^2$ liposomal irinotecan (free base) followed by the administration of 3 mg/kg nivolumab, once every two weeks for two weeks; and repeating said 28-day treatment cycle until a progression or an unacceptable toxicity is observed.

In certain embodiments, said schedule comprises administering to a human host during a 28-day treatment cycle: a total of 80 mg/m$^2$ liposomal irinotecan (free base) followed by the administration of 3 mg/kg nivolumab, once every two weeks for two weeks; and repeating said 28-day treatment cycle until a progression or an unacceptable toxicity is observed.

In certain embodiments, the cancer is selected from the group consisting of melanoma, pancreatic cancer, colorectal cancer, Hodgkin's lymphoma, NSCLC and RCC. In certain embodiments, the cancer is selected from the group consisting of melanoma, NSCLC and RCC. In particular embodiments, for example, the cancer is melanoma.

In certain embodiments, the liposomal irinotecan comprises liposomes having a unilamellar lipid bilayer vesicle, approximately 110 nm in diameter, which encapsulates an aqueous space containing irinotecan in a gelated or precipitated state as the sucrose octasulfate salt; wherein the vesicle is composed of 1,2-distearoyl-sn-glycero-3-phosphocholine (DSPC) 6.81 mg/mL, cholesterol 2.22 mg/mL, and methoxy-terminated polyethylene glycol (MW 2000)-distearoylphosphatidyl ethanolamine (MPEG-2000-DSPE) 0.12 mg/mL.

In certain embodiments, each mL also contains 2-[4-(2-hydroxyethyl) piperazin-1-yl]ethanesulfonic acid (HEPES) as a buffer 4.05 mg/mL and sodium chloride as an isotonicity reagent 8.42 mg/mL.

In certain embodiments, the host is human and is known not to be homozygous for the UGT1A1*28 allele.

In certain embodiments, the combination of the anti-neoplastic agent liposomal irinotecan and 3 mg/kg of the anti-neoplastic agent nivolumab is administered to a human host once every two weeks for a total of at least six weeks with each administration of liposomal irinotecan comprising the administration of a total of 43, 50, 70 or 80 mg/m$^2$ liposomal irinotecan (free base) followed by the administration of 3 mg/kg nivolumab on the same day as the liposomal irinotecan, and no other anti-neoplastic agents are administered during the six weeks.

In certain embodiments, provided herein is are methods of treatment of cancer in a host in need thereof comprising the administration of a combination of liposomal irinotecan and pembrolizumab, in an amount and in a schedule of administration that is therapeutically synergistic in the treatment of said cancer.

In certain embodiments, said schedule comprises administering to a human host during a 28-day treatment cycle: a total of 80 mg/m$^2$ liposomal irinotecan (free base) followed by the administration of 2 mg/kg pembrolizumab, once every two weeks for two weeks; and repeating said 28-day treatment cycle until a progression or an unacceptable toxicity is observed.

In certain embodiments, said schedule comprises administering to a human host during a treatment cycle: a total of 43, 50, 70 or 80 mg/m² liposomal irinotecan (free base) once every two weeks for two weeks and administration of 2 mg/kg pembrolizumab once every three weeks; and repeating said treatment cycle until a progression or an unacceptable toxicity is observed.

In certain embodiments, said schedule comprises administering to a human host during a treatment cycle: a total of 80 mg/m² liposomal irinotecan (free base) once every two weeks for two weeks and administration of 2 mg/kg pembrolizumab once every three weeks; and repeating said treatment cycle until a progression or an unacceptable toxicity is observed.

In certain embodiments, the cancer is selected from the group consisting of melanoma, pancreatic cancer, colorectal cancer, Hodgkin's lymphoma, NSCLC and RCC. In certain embodiments, the cancer is selected from the group consisting of melanoma, pancreatic cancer, NSCLC and RCC. In particular embodiments, for example, the cancer is melanoma.

In certain embodiments, the cancer is melanoma.

In certain embodiments, the liposomal irinotecan comprises liposomes having a unilamellar lipid bilayer vesicle, approximately 110 nm in diameter, which encapsulates an aqueous space containing irinotecan in a gelated or precipitated state as the sucrose octasulfate salt; wherein the vesicle is composed of 1,2-distearoyl-sn-glycero-3-phosphocholine (DSPC) 6.81 mg/mL, cholesterol 2.22 mg/mL, and methoxy-terminated polyethylene glycol (MW 2000)-distearoylphosphatidyl ethanolamine (MPEG-2000-DSPE) 0.12 mg/mL. MM-398

In particular embodiments of the above recited embodiments, no other antineoplastic agent is administered for the treatment of the cancer.

In certain embodiments, the method further comprises administering another therapeutic agent.

In some embodiments, the therapeutic agent is chosen from a taxane, inhibitor of bcr-abl, inhibitor of EGFR, DNA damaging agent, and antimetabolite. In particular embodiments, the therapeutic agent is chosen from aminoglutethimide, amsacrine, anastrozole, asparaginase, bcg, bicalutamide, bleomycin, buserelin, busulfan, campothecin, capecitabine, carboplatin, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, octreotide, oxaliplatin, paclitaxel, pamidronate, pentostatin, perifosine, plicamycin, porfimer, procarbazine, raltitrexed, rituximab, sorafenib, streptozocin, sunitinib, suramin, tamoxifen, temozolomide, temsirolimus, teniposide, testosterone, thioguanine, thiotepa, titanocene dichloride, topotecan, trastuzumab, tretinoin, vinblastine, vincristine, vindesine, and vinorelbine.

In some embodiments, the method further comprises administering non-chemical methods of cancer treatment. In particular embodiments, the method further comprises administering radiation therapy. In particular embodiments, the method further comprises administering surgery, thermoablation, focused ultrasound therapy, cryotherapy, or any combination thereof.

Also provided herein are embodiments equivalent to the methods above, disclosing the corresponding uses of a combination of liposomal irinotecan and nivolumab or liposomal irinotecan and pembrolizumab.

Compositions

The present disclosure provides a composition comprising an effective amount of a Topoisomerase I inhibitor and an α-PD-L1 or α-PD-1 antibody.

In some embodiments, the α-PD-L1 antibody is a humanized monoclonal antibody.

In some embodiments, the α-PD-1 antibody is chosen from nivolumab, and pembrolizumab.

In some embodiments, the Topoisomerase I inhibitor is chosen from irinotecan, topotecan, camptothecin and lamellarin D. In particular embodiments, the Topoisomerase I inhibitor is irinotecan.

Kits

The present disclosure provides a kit for treating a cancer in a subject in need thereof, comprising:
a. Topoisomerase I inhibitor and an α-PD-L1 or α-PD-1 antibody; and
b. written instructions for administering to the subject an effective amount of a Topoisomerase I inhibitor and an α-PD-L1 or α-PD-1 antibody to treat the cancer.

When the Topoisomerase I inhibitor and an α-PD-L1 or α-PD-1 antibody are administered simultaneously, the kit may contain the Topoisomerase I inhibitor and the α-PD-L1 or α-PD-1 antibody in a single pharmaceutical composition or in separate pharmaceutical compositions and packaged accordingly. When the Topoisomerase I inhibitor and the α-PD-L1 or α-PD-1 antibody are not administered simultaneously, the kit will contain Topoisomerase I inhibitor and the α-PD-L1 or α-PD-1 antibody in separate pharmaceutical compositions and packaged accordingly.

In one embodiment the kit comprises: a first container comprising the Topoisomerase I inhibitor in association with a pharmaceutically acceptable adjuvant, diluent or carrier; and a second container comprising the α-PD-L1 or α-PD-1 antibody in association with a pharmaceutically acceptable adjuvant, diluent or carrier. The kit can also provides instruction, such as dosage and administration instructions. Such dosage and administration instructions can be of the kind that are provided to a doctor, for example by a drug product label, or they can be of the kind that are provided by a doctor, such as instructions to a patient.

Formulation

The compositions of the present disclosure may be administered in any way which is medically acceptable which may depend on the condition or injury being treated. Possible administration routes include injections, by parenteral routes such as intramuscular, subcutaneous, intravenous, intraarterial, intraperitoneal, intraarticular, intraepidural, intrathecal, or others, as well as oral, nasal, ophthalmic, rectal, vaginal, topical, or pulmonary, e.g., by inhalation. For the delivery of liposomally drugs formulated according to the invention, to tumors of the central nervous system, a slow, sustained intracranial infusion of the liposomes directly into the tumor (a convection-enhanced delivery, or CED) is of particular advantage. See Saito, et al., Cancer Research, vol. 64, p. 2572-2579, 2004; Mamot, et al., J. Neuro-Oncology, vol. 68, p. 1-9, 2004. The compositions may also be directly applied to tissue surfaces. Sustained release, pH dependent release, or other specific chemical or environmental condition mediated release administration is also specifically included in the invention, e.g., by such means as depot injections, or erodible implants. Suitable compositions for oral administration include solid formulations such as tablets, lozenges and capsules, which can contain liquids, gels, or powders. Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents. Preparation of pharmaceutically acceptable formulations can be accomplished according to methods known in the art.

Dosage and Administration

Compositions of the present disclosure may be administered in a single dose or in multiple doses to achieve an effective treatment objective. Typically the dosages for the liposome pharmaceutical composition of the present invention are a therapeutically effective dose in a range between about 0.005 and about 500 mg of the therapeutic entity per kilogram of body weight, most often, between about 0.1 and about 100 mg therapeutic entity/kg of body weight.

An anti-PD-1 antibody is administered at a dosage amount of from 2 mg/kg to 30 mg/kg every two to three weeks; suitably, from 3 mg/kg to 20 mg/kg every two to three weeks; suitably, 5 mg/kg to 10 mg/kg every two to three weeks; suitably, 6 mg/kg every two to three weeks. In certain embodiments, anti-PD-1 antibody is administered as above every two weeks. In certain embodiments, anti-PD-1 antibody is administered as above every three weeks.

Typically, the liposome pharmaceutical compositions of the present invention are prepared as a topical or an injectable, either as a liquid solution or suspension. However, solid forms suitable for solution in, or suspension in, liquid vehicles prior to injection can also be prepared. The composition can also be formulated into an enteric-coated tablet or gel capsule according to known methods in the art.

The liposome composition of the present invention can be administered in any way which is medically acceptable which may depend on the condition or injury being treated. Possible administration routes include injections, by parenteral routes such as intramuscular, subcutaneous, intravenous, intraarterial, intraperitoneal, intraarticular, intraepidural, intrathecal, or others, as well as oral, nasal, ophthalmic, rectal, vaginal, topical, or pulmonary, e.g., by inhalation. For the delivery of liposomally drugs formulated according to the invention, to tumors of the central nervous system, a slow, sustained intracranial infusion of the liposomes directly into the tumor (a convection-enhanced delivery, or CED) is of particular advantage. See Saito, et al., Cancer Research, vol. 64, p. 2572-2579, 2004; Mamot, et al., J. Neuro-Oncology, vol. 68, p. 1-9, 2004. The compositions may also be directly applied to tissue surfaces. Sustained release, pH dependent release, or other specific chemical or environmental condition mediated release administration is also specifically included in the invention, e.g., by such means as depot injections, or erodible implants. The quantity of liposome pharmaceutical composition necessary to deliver a therapeutically effective dose can be determined by routine in vitro and in vivo methods, common in the art of drug testing. See, for example, D. B. Budman, A. H. Calvert, E. K. Rowinsky (editors). Handbook of Anticancer Drug Development, LWW, 2003. Therapeutically effective dosages for various therapeutic entities are well known to those of skill in the art; and according to the present invention a therapeutic entity delivered via the pharmaceutical liposome composition of the present invention provides at least the same, or 2-fold, 4-fold, or 10-fold higher activity than the activity obtained by administering the same amount of the therapeutic entity in its routine non-liposome formulation.

According to the present invention, a desired entity can be loaded or entrapped into the liposomes by incubating the desired entity with the liposomes of the present invention in an aqueous medium at a suitable temperature, e.g., a temperature above the component lipids' phase transition temperature during loading while being reduced below the phase transition temperature after loading the entity. The incubation time is usually based on the nature of the component lipids, the entity to be loaded into the liposomes, and the incubation temperature. Typically, the incubation times of few minutes to several hours are sufficient. Because high entrapment efficiencies of more than 85%, typically more than 90%, are achieved, there is usually no need to remove unentrapped entity. If there is such a need, however, the unentrapped entity can be removed from the composition by various mean, such as, for example, size exclusion chromatography, dialysis, ultrafiltration, adsorption, or precipitation. It was unexpectedly found that maintaining of the low ionic strength during the incubation of an entity, such as, in particular, a camptothecin derivative or a vinca alkaloid derivative, with the liposomes of the present invention, followed by the increase in ionic strength at the end of the incubation, results in higher loading efficiency, better removal of unentrapped drug, and better liposome stability against aggregation. Typically, the incubation is conducted, e.g., in an aqueous solution, at the ionic strength of less than that equivalent to 50 mM NaCl, or more preferably, less than that equivalent to 30 mM NaCl. Following the incubation, a concentrated salt, e.g., NaCl, solution may be added to raise the ionic strength to higher than that of 50 mM NaCl, or more preferably, higher than that of 100 mM NaCl. Without being bound by a theory, we hypothesize that the increase of ionic strength aids dissociation of the entity from the liposome membrane, leaving substantially all entity encapsulated within the liposomal interior space.

In general, the entity-to-lipid ratio, e.g., drug load ratio obtained upon loading an entity depends on the amount of the entity entrapped inside the liposomes, the concentration of entrapped substituted ammonium and/or polyanion, e.g., salt, the physicochemical properties of the entrapped entity and the type of counter-ion (anion), e.g., polyanion used. Because of high loading efficiencies achieved in the compositions and/or by the methods of the present invention, the entity-to-lipid ratio for the entity entrapped in the liposomes is over 80%, over 90%, and typically more than 95% of the entity-to-lipid ratio calculated on the basis of the amount of the entity and the liposome lipid taken into the loading process (the "input" ratio). Indeed, practically 100% (quantitative) encapsulation is common. The entity-to lipid ratio in the liposomes can be characterized in terms of weight ratio (weight amount of the entity per weight or molar unit of the liposome lipid) or molar ratio (moles of the entity per weight or molar unit of the liposome lipid). One unit of the entity-to-lipid ratio can be converted to other units by a routine calculation, as exemplified below. The weight ratio of an entity in the liposomes of the present invention is typically at least 0.05, 0.1, 0.2, 0.35, 0.5, or at least 0.65 mg of the entity per mg of lipid. In terms of molar ratio, the entity-to-lipid ratio according to the present invention is at least from about 0.02, to about 5, preferably at least 0.1 to about 2, and more preferably, from about 0.15 to about 1.5 moles of the drug per mole of the liposome lipid. In one embodiment, the entity-to-lipid ratio, e.g., drug load ratio of camptothecin derivatives is at least 0.1, e.g., 0.1 mole of camptothecin derivative per one mole of liposome lipid, and preferably at least 0.2. In another embodiment, the entity-to-lipid ratio, e.g., drug load is at least about 300 mg entity (e.g., vinca alkaloid or a derivative thereof per mg of liposome-forming lipid. In yet another embodiment, the entity-to-lipid ratio, e.g., drug load is at least about 500 mg entity (e.g. camptothecin derivative or camptothecin prodrug) per mg of liposome-forming lipid. Surprisingly, the invention afforded stable and close to quantitative liposomal encapsulation of a camptothecin derivative drug, e.g., irinotecan, at the drug-to-lipid ratio of over 0.8 mmol of the entity per 1 g of liposome lipid, over 1.3 mmol of entity per 1 g of liposome lipid, and even at high as 1.7 mmol entity per 1 g liposome lipid (see Example 74).

If the liposome comprises a phospholipid, it is convenient to express the entity content in the units of weight (mass) amount of the drug per molar unit of the liposome phospholipid, e.g., mg drug/mmol of phospholipid. However, a person skilled in the art would appreciate that the drug content can be equivalently expressed in a manner independent of the presence of phospholipids in a liposome, and furthermore, can be equivalently expressed in terms of a molar amount of the drug per unit (mass or molar) of the liposome lipid content. For example, a liposome containing 3 molar parts of distearoylphosphatidylcholine (DSPC, molecular weight 790), 2 molar parts of cholesterol (molecular weight 387), and 0.015 molar parts of poly(ethylene glycol)-derivatized distearoylphosphatidylethanolamine (PEG-DSPE, molecular weight 2750), and containing a drug doxorubicin (molecular weight 543.5) at the drug/lipid ratio of 150 mg/mmol phospholipid, the same drug content can be equivalently expressed in terms of mg drug/mg total lipid as follows:

(a) Calculate the molar amounts of liposome lipid components normalized to the molar unit of liposome phospholipids (DSPC and PEG-DSPE in this example) by dividing the molar quantity of a component by the total of the molar quantities of the liposome phospholipids:
DSPC 3/(3+0.015)=0.99502
Cholesterol 2/(3+0.015)=0.66335
PG-DSPE 0.015/(3+0.015)=0.00498

(b) Calculate the mass amount of total liposome lipid corresponding to a unit molar amount of liposome phospholipid and the components molecular weights:
Total lipid, mg/mmol phospholipid=0.99502×790+ 0.66335×387+0.00498×2750=1056.48

(c) Calculate the mass amount of drug per mass unit of total lipid by dividing the drug content expressed in mass units per molar unit of phospholipid by the number obtained in step (b):
Doxorubicin, mg/mg total lipid=150/1056.48=0.14198.

(d) Calculate the molar amount of the drug per unit mass of total lipid by dividing the number obtained in step (c) by the drug molecular weight (in this case, 543.5):
Doxorubicin, mmol/g total lipid=0.14198/543.5× 1000=0.261.

(e) Calculate the molar part of phospholipids in the liposome lipid matrix:
Phospholipid molar part=(total moles of phospholipids)/ (total moles amount of lipids)=(3+0.015)/(3+2+ 0.015)=0.6012.

(f) Calculate the molar ratio of doxorubicin to total lipid.
Doxorubicin, mol/mol of total lipid=(Phospholipid molar part)×(Doxorubicin, g/mole phospholipid)/(Doxorubicin molecular weight)=0.6012×150/543.5=0.166

Thus, the relationship between drug-to-lipid and drug-to-phospholipid ratio expressed in various units is readily established. As used herein, a 'lipid' includes, without limitation, any membrane-forming components of the liposome membrane, such as, for example, polymers and/or detergents. See, for example: U.S. Pat. No. 8,147,867 which is incorporated herein by reference in its entirety for all purposes.

Unless otherwise indicated herein, the dose of a MM-398 irinotecan liposome is refers to the equivalent amount of irinotecan hydrochloride trihydrate. For example, a 120 mg dose of MM-398 irinotecan liposome contains an amount of irinotecan present in 120 mg of irinotecan hydrochloride trihydrate. Converting a dose based on irinotecan hydrochloride trihydrate to a dose based on irinotecan free base is accomplished by substituting the molecular weight of irinotecan hydrochloride trihydrate (677.19 g/mole) with the molecular weight of irinotecan free base (586.68 g/mole), which results in a conversion factor of 0.866.

In order that the disclosure described herein may be more fully understood, the following examples are set forth. It should be understood that these examples are for illustrative purposes only and are not to be construed as limiting this disclosure in any manner.

Biological Assays

Synergistic Effect of Top 1 Inhibitors on T-cell mediated killing of Melanoma 2338 and 2400 Cells. The patient derived melanoma cell lines 2338 and 2400 were treated with autologous tumor infiltrating lymphocytes (TILs) at varying effector T cell to tumor cell (E:T) ratios for 3 h. Cells were then stained for activated caspase 3, to quantify apoptosis by flow cytometry. 2338 and 2400 cells were treated with the Top1 inhibitor SN38 for 24 h using a concentration range of 0.125-1.0 uM. Cells were then stained for activated caspase 3, or drug treated cells were washed and then incubated with autologous TILs for 3 h.

Figure 2A:
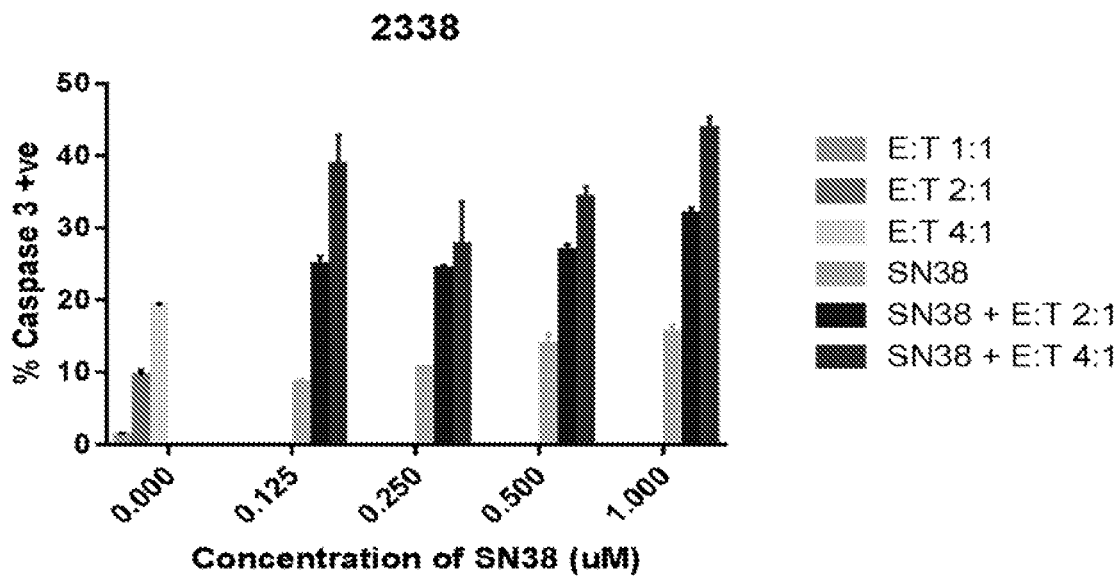
FIG. 2 depicts the synergistic effect of Top 1 inhibitors (TILs) on T-cell mediated killing of melanoma cells from patient derived melanoma cell lines 2338 (FIG. 2A, top) and 2400 (FIG. 2B, bottom) by treatment with autologous TILs at varying effector T cell to tumor cell (E:T) ratios for 3 hours, as measured by percent activated caspase 3.

Apoptosis was then quantified via a high throughput caspase 3-based cytotoxicity assay. Human melanoma cells were stained with DDAO dye and either: (i) seeded for 24 h in 96 well plates with 1 uM of each of the 850 compounds in our screen or DMSO as a control, (ii) seeded for 24 h and then incubated with autologous T cells for 3 h, or (iii) seeded for 24 h with 1 uM compound, washed and then incubated with autologous T cells for 3 h. Cells were then washed, fixed, permeabilized and stained for activated caspase 3. Flow cytometry was used to quantify staining as a measure of apoptosis. Results are given in FIGS. 2A and 2B.

The data shown in FIG. 2 were analyzed in Calcusyn to compute the Combination Index (CI) of combining SN38 with 2338 and 2400 TILs. The CIs of 2338 and 2400 are represented in the normalized isobolograms in FIGS. 3A and 3B respectively. Calcusyn is based on the Chou-Talalay method of quantifying synergy where synergism is CI<1 (points below the diagonal line), additive effect is CI=1 (points on the diagonal line), and antagonism is CI>1 (points above the diagonal line). See, e.g., Chou, T. C., "Drug combination studies and their synergy quantification using the Chou-Talalay method," *Cancer research* 70, 440-446 (2010).

In vivo anti-tumor response with the Top1 inhibitor nal-IRI (MM-398) is significantly higher in comparison to free irinotecan. In a first experiment, C57BL/6 mice were injected subcutaneously with $5 \times 10^5$ MC38/gp100 cells.

Figure 4A:
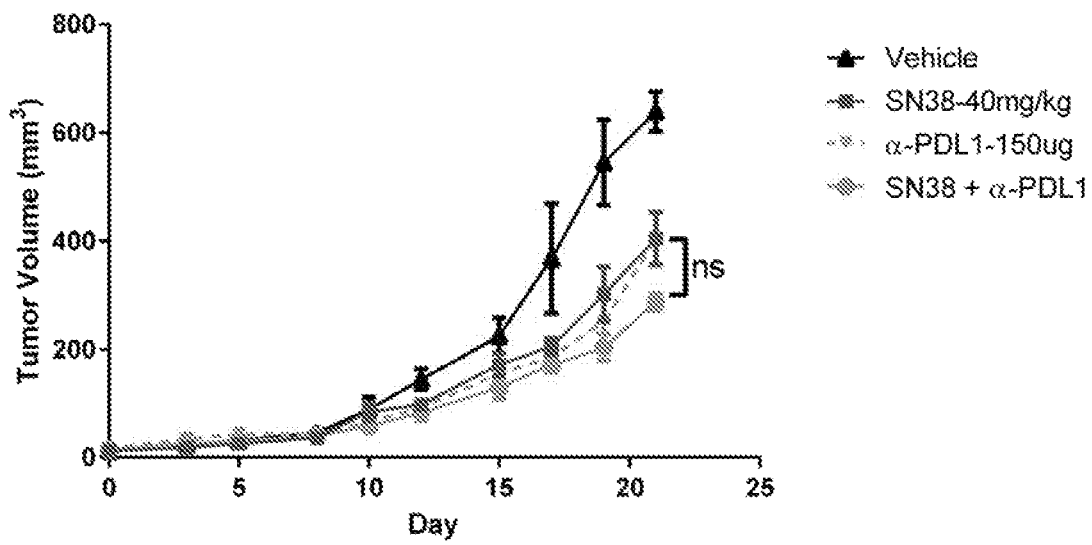
FIG. 4A shows that the combination of SN38 and α-PD-L1 trended better than SN38 or α-PD-L1 alone, but not significantly.
Figure 4B:
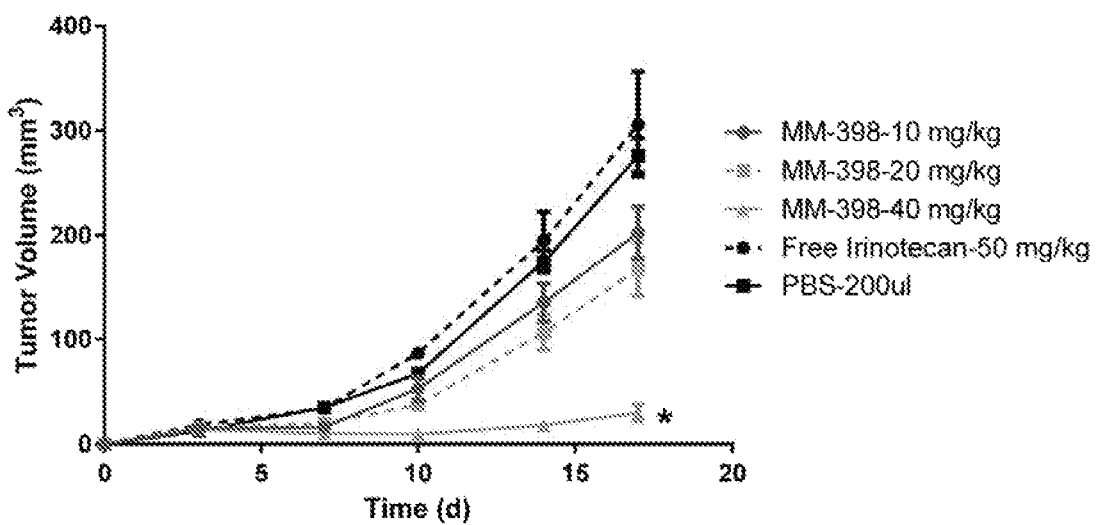
FIG. 4B shows that in vivo anti-tumor response with MM-398 is significantly higher in comparison to free irinotecan, and that efficacy increases with dose (wherein * indicates P<0.0001).

Mice were treated with 40 mg/kg SN38 (3 times weekly intraperitoneally), 150 ug α-PD-L1 (mouse PD-L1-PE (clone 10F.9G2) obtained from Bio X Cell, 10 Technology Dr., Suite 2B, West Lebanon, N.H. 03784-1671 USA) (every 3 days intraperitoneally), or a combination of SN38 and α-PD-L1. Control group received phosphate-buffered saline (PBS) and Rat IgG2B control antibody. Mice were treated for 3 weeks. Results are shown in FIG. 4A, which shows that the combination of SN38 and α-PD-L1 trended better than SN38 or α-PD-L1 alone, but not significantly. In a second experiment, C57BL/6 mice were injected subcutaneously with $5 \times 10^5$ MC38/gp100 cells. Three days later when tumors were palpable, mice were randomized into treatment groups (n=5). Beginning on day 3, mice received nal-IRI (MM-398, intravenously), free irinotecan (intraperitoneally), or PBS (intravenously) as the vehicle, once weekly for 3 weeks. Results are shown in FIG. 4B, which demonstrates that MM-398 was better at all doses than free irinotecan, and was increasingly efficacious as the dose increased (achieving significance at 40 mg/kg.

Figure 2B:
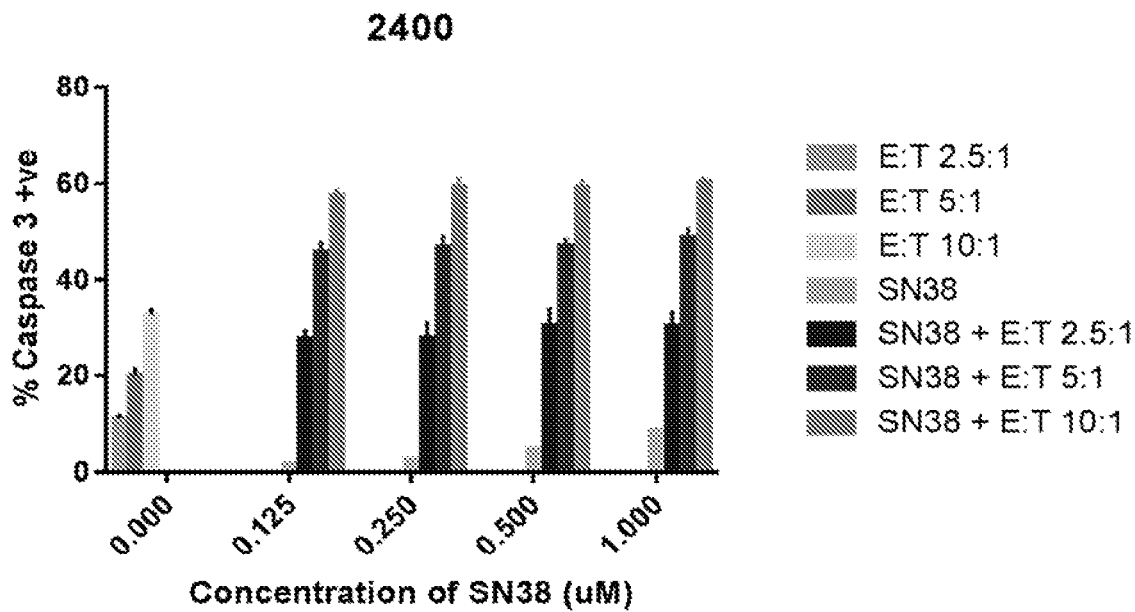
Figure 3A:
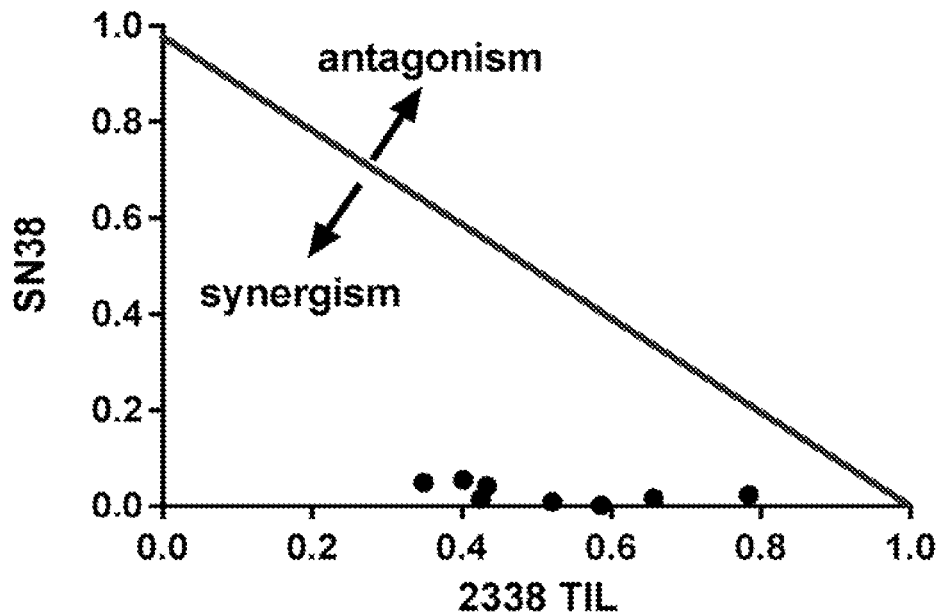
FIG. 3A is a normalized isobologram of the Combination Index (CI) of combining SN38 with 2338 TIL.
Figure 3B:
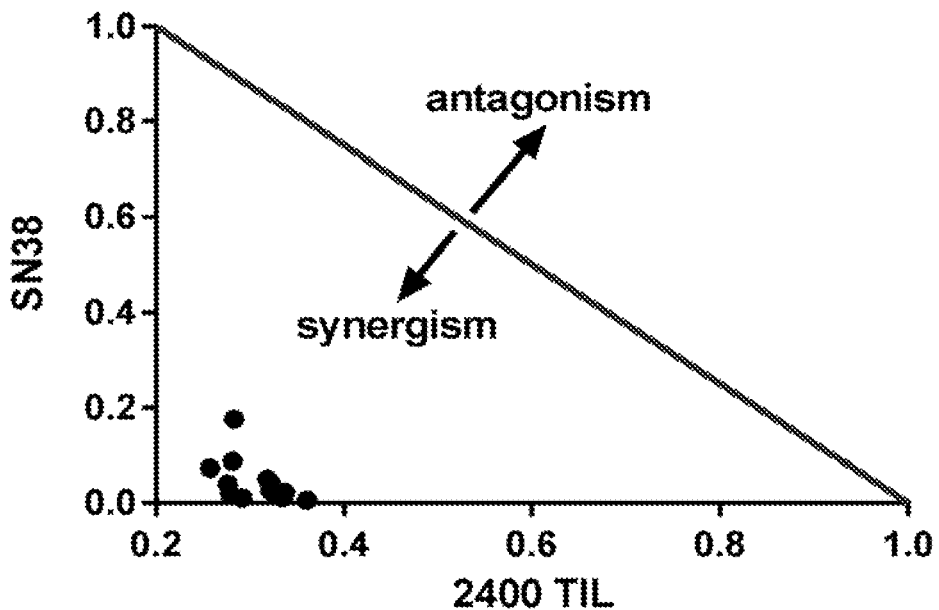
FIG. 3B is a normalized isobologram of the Combination Index (CI) of combining SN38 with 2400 TIL.
Figure 5A:
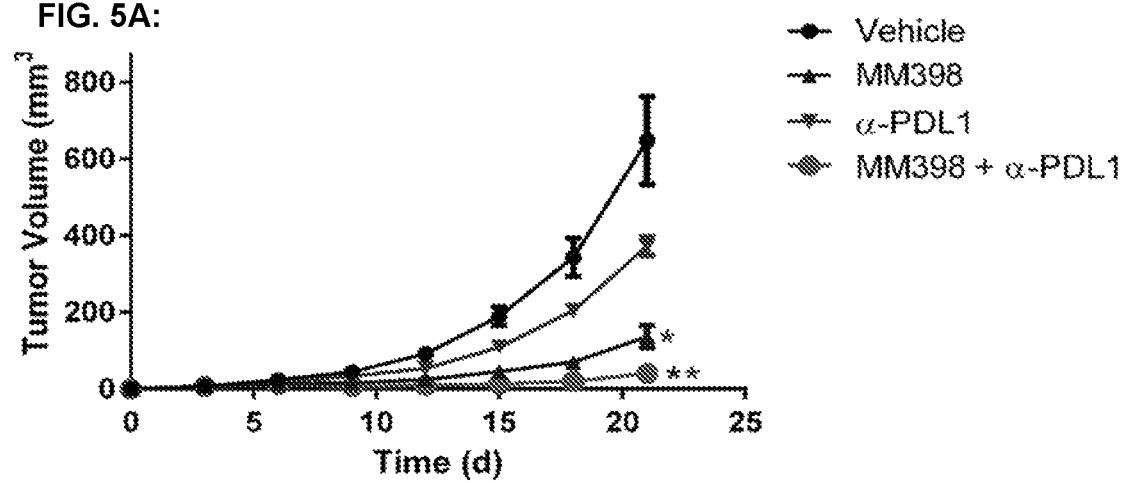
FIG. 5A is a graph of measured tumor volume over time after administration of MM-398 liposomal irinotecan and the anti-PD-L1 antibody described in the Table 2 of Example 3 in a mouse xenograft model.

In vivo anti-tumor response and survival are increased when nanoliposomal irinotecan, nal-IRI (MM-398) is combined with α-PD-L1 antibody. In a first experiment, C57BL/6 mice were injected s.c. with $5 \times 10^5$ MC38/gp100 cells. Three days later when tumors were palpable, mice were randomized into treatment groups (n=5) receiving nal-IRI (40 mg/kg), α-PD-L1 antibody (mouse PD-L1-PE (clone 10F.9G2) obtained from Bio X Cell, 10 Technology Dr., Suite 2B, West Lebanon, N.H. 03784-1671 USA) (150 ug/mouse), or both nal-IRI and α-PD-L1 antibody. Vehicle control group received PBS and isotype-matched control antibody Rat IgG2b (150 ug). Beginning on day 3, mice received once weekly doses of nal-IRI and antibody was administered every 3 days. FIG. 5A shows tumor volume up to day 21; FIG. 2B shows tumor survival data for mice treated with MM-398 or α-PD-L1 antibody alone, or a combination of both agents.

Gene expression changes in antigen processing genes after Top1 inhibition. RNA was isolated from patient derived melanoma cell lines treated with SN38 or DMSO as a control. The heatmap in FIG. 6A represents the differential expression of a subset of genes involved in antigen presentation. FIG. 6A is a subset of the data of the microarray analysis that was performed on SN38-treated tumor cells described in Example 5. This subset of the data focused on the differential expression changes of genes involved in antigen processing and presentation in tumor cells. Antigen processing and presentation is a fundamental step in the cancer immunity cycle that allows for the recognition of tumor cells by cytolytic T cells. We observed significant upregulation in the expression of MHC Class I (HLA-A, B, C) and in Beta-2-microglobulin (B2M) and the transporter proteins TAP and TAP binding protein (TAPBP), all crucial for the antigen processing and presentation pathway. This data suggests that one way by which Top1 inhibitor-treatment of melanoma tumor cells may improve T cell mediated killing is by increasing antigen processing and presentation, which may allow for increased recognition and targeting by T cells, and subsequent greater induction of tumor cell killing.

Figure 14:
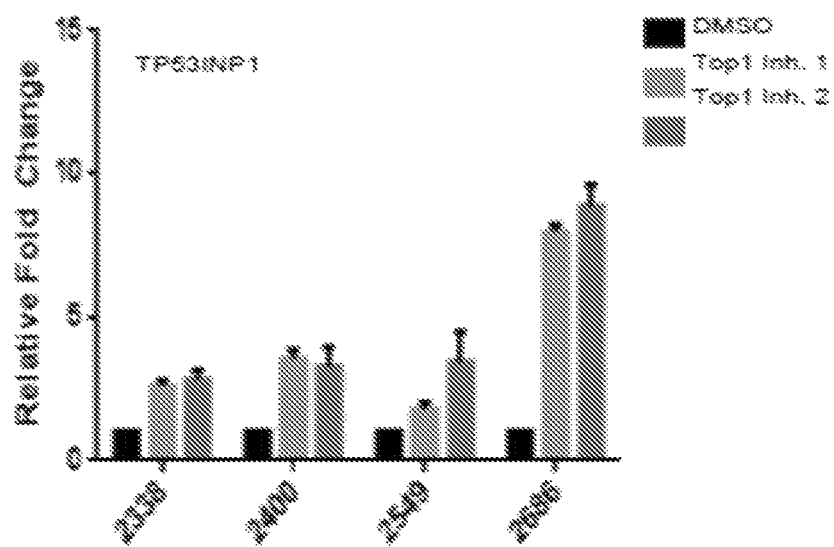
FIG. 14 is a graph showing the change in TP53INP1 following Top1 inhibition.

Referring to FIGS. 6B and 14: the heatmap in FIG. 6B represents a subset of genes differentially expressed after Top1 inhibition from microarray analysis. The data shown represents a portion of the gene expression analysis which was described in Example 5. This portion of the data focuses on the differential expression of some genes related to p53 signaling. In particular, we have chosen to focus on TP53INP1 (or Teap), which is a p53 regulatory gene shown to be involved in directing an apoptotic response in tumor cells (Gironella et al., *Natl Acad Sci* USA 2007; Tomasini et al., *J Biol Chem* 2001). We observed a significant upregulation in the expression of Teap with SN38 treatment in melanoma. This phenotype was also validated by quantitative real time PCR (qRT-PCR) performed on a number of melanoma patient-derived tumor cell lines treated with 2 different Top1 inhibitors (Top1 inh. 1=SN38, Top1 inh. 2=Topotecan).

Figure 7:
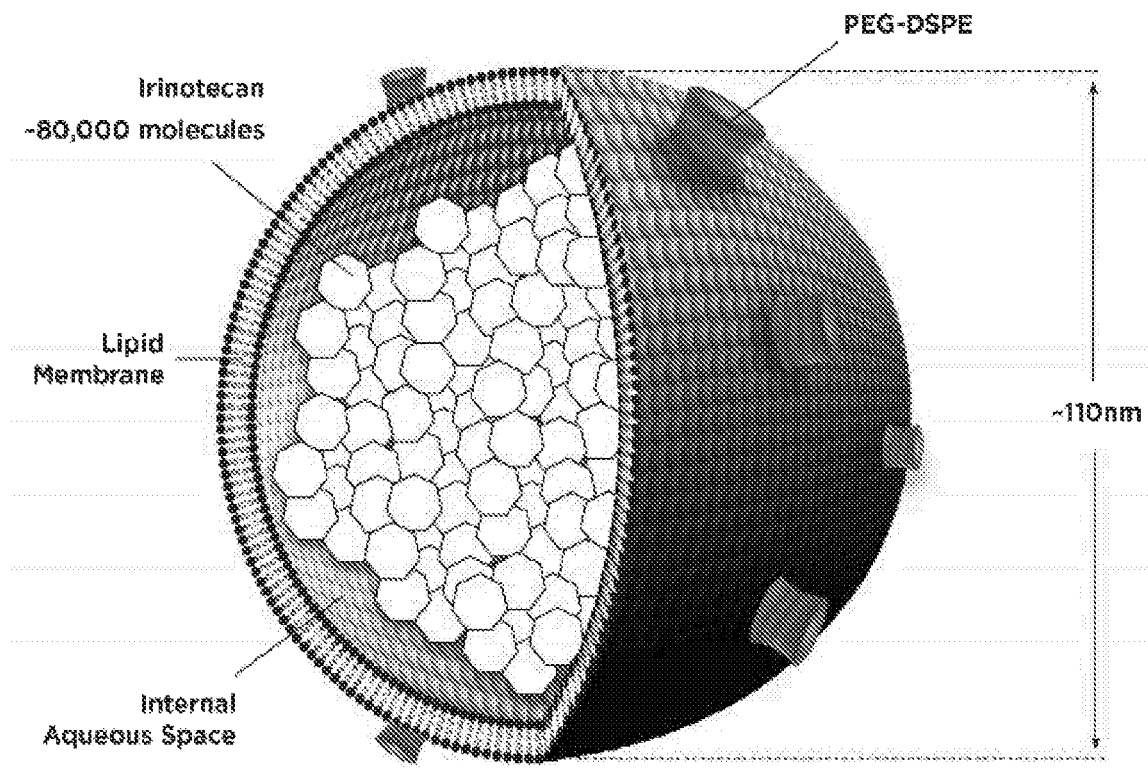
FIG. 7 shows Nano-liposomal irinotecan (nal-IRI), MM-398.

Unless otherwise indicated, the nano-liposomal irinotecan material used where indicated by corresponding the data in the Figures comprises irinotecan sucrose octasulfate encapsulated in a liposome as depicted in FIG. 7. FIG. 7 shows Nano-liposomal irinotecan (nal-IRI), MM-398. MM-398 irinotecan sucrose octasulfate salt liposome injection may also be referred to as irinotecan HCl liposome injection because irinotecan HCl (trihydrate) is the active pharmaceutical ingredient that is used to load irinotecan into liposomes containing triethylammonium sucrose octasulfate to prepare MM-398 liposomes. This nomenclature may be used even though the hydrochloride ion of the irinotecan HCl reacts with the triethylammonium ion of the triethylammonium sucrose octasulfate to yield triethylammonium chloride (triethylamine hydrochloride), leaving irinotecan sucrose octasulfate salt as the entrapped pharmaceutical agent within the MM-398 liposomes. Further details about irinotecan liposomes are provided in the publication WO2013/188586, filed Jun. 12, 2013 (incorporated by reference herein in its entirety).

The liposomal irinotecan comprises liposomes having a unilamellar lipid bilayer vesicle, approximately 110 nm in diameter, which encapsulates an aqueous space containing irinotecan in a gelated or precipitated state as the sucrose octasulfate salt; wherein the vesicle is composed of 1,2-distearoyl-sn-glycero-3-phosphocholine (DSPC) 6.81 mg/mL, cholesterol 2.22 mg/mL, and methoxy-terminated polyethylene glycol (MW 2000)-distearoylphosphatidyl ethanolamine (MPEG-2000-DSPE) 0.12 mg/mL. Each mL can also contain 2-[4-(2-hydroxyethyl) piperazin-1-yl]ethanesulfonic acid (HEPES) as a buffer 4.05 mg/mL and sodium chloride as an isotonicity reagent 8.42 mg/mL.

As provided herein, irinotecan can be administered in a stable liposomal formulation as irinotecan sucrose sulfate liposome injection (otherwise termed "irinotecan sucrose octasulfate salt liposome injection" or "irinotecan sucrosofate liposome injection"), the formulation referred to herein as "MM-398" (also known as PEP02, see U.S. Pat. No. 8,147,867). MM-398 may be provided as a sterile, injectable parenteral liquid for intravenous injection. The required amount of MM-398 may be diluted, e.g. in 500 mL of 5% dextrose injection USP and infused over a 90 minute period.

An MM-398 liposome is a unilamellar lipid bilayer vesicle of approximately 80-140 nm in diameter that encapsulates an aqueous space which contains irinotecan complexed in a gelated or precipitated state as a salt with sucrose octasulfate. The lipid membrane of the liposome is composed of phosphatidylcholine, cholesterol, and a polyethyleneglycol-derivatized phosphatidyl-ethanolamine in the amount of approximately one polyethyleneglycol (PEG) molecule for 200 phospholipid molecules.

This stable liposomal formulation of irinotecan has several attributes that may provide an improved therapeutic index. The controlled and sustained release improves activity of this schedule-dependent drug by increasing duration of exposure of tumor tissue to drug, an attribute that allows it to be present in a higher proportion of cells during the S-phase of the cell cycle, when DNA unwinding is required as a preliminary step in the DNA replication process. The long circulating pharmacokinetics and high intravascular drug retention in the liposomes can promote an enhanced permeability and retention (EPR) effect. EPR allows for deposition of the liposomes at sites, such as malignant tumors, where the normal integrity of the vasculature (capillaries in particular) is compromised resulting in leakage out of the capillary lumen of particulates such as liposomes. EPR may thus promote site-specific drug delivery of liposomes to solid tumors. EPR of MM-398 may result in a subsequent depot effect, where liposomes accumulate in tumor associated macrophages (TAMs), which metabolize irinotecan, converting it locally to the substantially more cytotoxic SN-38. This local bioactivation is believed to result in reduced drug exposure at potential sites of toxicity and increased exposure at cancer cells within the tumor.

Irinotecan is converted to SN-38 within the body upon release from a MM-398 liposome. The metabolic transformation of MM-398 to SN-38 (e.g. in plasma) includes two comprising 400 mg/m$^2$ of the (l+d) racemic form. In various embodiments the liposomal irinotecan is MM-398.

One method of treating cancer comprises the administration of 60-120 mg/m$^2$ of MM-398 liposomal irinotecan (i.e., a dose of MM-398 containing the amount of irinotecan corresponding to 60-120 mg/m$^2$ of irinotecan hydrochloride trihydrate) having a half-life of at least about 24 hours, in combination with the administration of 3 mg/kg of checkpoint inhibitor antibody that binds to anti-PD1. For example, the MM-398 liposomal irinotecan can be administered at a dose of 60, 80 or 120 mg/m$^2$ every 2 weeks. The antibody can be nivolumab administered over 60 minutes every 2 weeks. Optionally, the method further includes administration of 5-fluorouracil (e.g., 2,400 mg/m$^2$) and leucovorin (e.g., 200 mg/m$^2$ of the 1-form or 400 mg/m$^2$ of the 1+d racemic form) in combination with the MM-398, and prior to administration of the checkpoint inhibitor antibody. When administered once every two weeks at 80 mg/m$^2$ (hydrochloride trihydrate basis, equivalent to 70 mg/$^{m2}$ free base), MM-398 has the mean (+/−standard deviation) total irinotecan and total SN-38 in Table 1 below.

TABLE 1

| | Total Irinotecan | | | | | Total SN-38 | | |
|---|---|---|---|---|---|---|---|---|
| Dose (mg/m$^2$) | $C_{max}$ [μg/mL] (n = 25) | AUC$_{0-\infty}$ [h · μg/mL] (n = 23) | $t_{1/2}$ [h] (n = 23) | CL [L/h] (n = 23) | $V_d$ [L] (n = 23) | $C_{max}$ [ng/mL] (n = 25) | AUC$_{0-\infty}$ [h · ng/mL] (n = 13) | $t_{1/2}$ [h] (n = 13) |
| 70 | 37.2 (8.8) | 1364 (1048) | 25.8 (15.7) | 0.20 (0.17) | 4.1 (1.5) | 5.4 (3.4) | 620 (329) | 67.8 (44.5) |

$C_{max}$: Maximum plasma concentration
AUC$_{0-\infty}$: Area under the plasma concentration curve extrapolated to time infinity
$t_{1/2}$: Terminal elimination half-life
CL: Clearance
$V_d$: Volume of distribution steps: (1) the release of irinotecan from the liposome and (2) the conversion of free irinotecan to SN-38. While not intending to be limited by theory, it is believed that once irinotecan leaves the liposomes, it is catabolized by the same metabolic pathways as conventional (free) irinotecan. Therefore the genetic polymorphisms in humans predictive for the toxicity and efficacy of irinotecan and those of MM-398 can be considered similar. Nonetheless, in the MM-398 formulation compared to free irinotecan, the deficient genetic polymorphisms may show less association with severe adverse events and/or efficacy.

Liposomal irinotecan can be administered intravenously, either alone or in combination with 5-fluorouracil (5-FU) and/or leucovorin, prior to administration of an anti-PDL-1 antibody. In one embodiment, liposomal irinotecan is administered (alone or in combination with or prior to 5-FU and leucovorin) and prior to a checkpoint inhibitory antibody (e.g., an antibody binding to anti-PD 1). In another embodiment, the liposomal irinotecan is administered as part of a treatment cycle comprising the administration of a therapeutically effective dose of MM-398, followed by administration of leucovorin and 5-FU as a series of infusions over a total time period of about 48 hours. The liposomal irinotecan treatment cycle can be followed by administration of the checkpoint inhibitory antibody. For example, liposomal irinotecan can be administered intravenously over 90 minutes, leucovorin can be administered over 30 minutes, and 5-FU can be administered intravenously over 46 hours. Leucovorin can administered intravenously over 30 minutes, as a composition comprising about 200 mg/m$^2$ of the active (1) form or as a composition In a particular example, a method of treating cancer comprises administering by infusion to the patient in need thereof once every three weeks (a) a liposomal irinotecan treatment cycle comprising or consisting of a dose of 120 mg/m$^2$ MM-398 over 90 minutes, followed by the leucovorin over 30 minutes, followed by the 5-fluorouracil over 46 hours; followed by (b) a checkpoint antibody treatment cycle comprising an antibody that binds to anti-PD1 (e.g., 3 mg/kg of nivolumab administered over 60 minutes). A therapeutically effective time period can be selected between administration of the liposomal irinotecan treatment cycle and the checkpoint antibody treatment cycle. When administered once every three weeks at 120 mg/m$^2$, MM-398 has an AUC$_{0-1}$ of total irinotecan in blood that is 1,652 hr·ug/ml (120 mg/m$^2$) and SN38, the active metabolite, is 476 hr·ng/ml, and $T_{1/2}$ of total irinotecan in blood is 21.2 h and SN38 is 88.8 h.

In another particular example, a method of treating cancer comprises administering by infusion to the patient in need thereof (a) a liposomal irinotecan treatment cycle comprising or consisting of a dose of 80 mg/m$^2$ MM-398 over 90 minutes, followed by the leucovorin over 30 minutes, followed by the 5-fluorouracil over 46 hours; followed by (b) a checkpoint antibody treatment cycle comprising an antibody that binds to anti-PD1 (e.g., 3 mg/kg of nivolumab administered over 60 minutes). A therapeutically effective time period can be selected between administration of the liposomal irinotecan treatment cycle and the checkpoint antibody treatment cycle.

In one particular example, a method of treating cancer comprises administering by infusion to the patient in need thereof (a) a liposomal irinotecan treatment cycle comprising or consisting of a dose of 60 mg/m² MM-398 over 90 minutes, followed by the leucovorin over 30 minutes, followed by the 5-fluorouracil over 46 hours; followed by (b) a checkpoint antibody treatment cycle comprising an antibody that binds to anti-PD1 (e.g., 3 mg/kg of nivolumab administered over 60 minutes). A therapeutically effective time period can be selected between administration of the liposomal irinotecan treatment cycle and the checkpoint antibody treatment cycle One method of treating cancer comprises the administration of 60-120 mg/m² of liposomal irinotecan octasulfate (containing an amount of irinotecan equivalent to 60-120 mg/m² of irinotecan hydrochloride trihydrate) having an irinotecan half-life of at least about 24 hours in combination with the administration of 3 mg/kg of a checkpoint inhibitor antibody such as nivolumab. For example, the MM-398 can be administered at a dose of 60, 80 or 120 mg/m² every 2 weeks. The nivolumab can be administered over 60 minutes every 2 weeks.

Other Embodiments

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

Also provided are embodiments wherein any of embodiment above may be combined with any one or more of these embodiments, provided the combination is not mutually exclusive. As used herein, two embodiments are "mutually exclusive" when one is defined to be something which cannot overlap with the other.

In some embodiments, a method of killing cancer cells in a biological sample can comprise contacting the biological sample with an effective amount of a Topoisomerase I inhibitor and an α-PD-L1 antibody. These or other embodiments can be characterized by one or more of the following, alone or in any combination:
- the α-PD-L1 or α-PD-1 antibody can be a humanized monoclonal antibody;
- the subject can be a human;
- the cancer can be chosen from skin cancer, pancreatic cancer, or a variant thereof;
- the administration of the Topoisomerase I inhibitor and α-PD-L1 or α-PD-1 antibody can be sequential;
- the administration of the Topoisomerase I inhibitor occurs before administration of the α-PD-L1 or α-PD-1 antibody;
- the administration of the α-PD-L1 or α-PD-1 antibody can occur before administration of the Topoisomerase I inhibitor, or the administration of the α-PD-L1 or α-PD-1 antibody and Topoisomerase I inhibitor can be essentially simultaneous;
- the α-PD-L1 antibody can be chosen from nivolumab and pembrolizumab;
- the Topoisomerase I inhibitor is chosen from irinotecan, topotecan, camptothecin and lamellarin D, or liposomal formulations thereof, or preferably the Topoisomerase I inhibitor is a liposomal irinotecan, or the irinotecan is provided in a composition comprising liposomes in an aqueous medium, the liposomes having an interior aqueous space separated from the aqueous medium by a membrane, the membrane comprising lipids, the lipids comprising an uncharged lipid component and a neutral phospholipid, with, entrapped inside the liposomes: irinotecan and sucrose octasulfate, or irinotecan and sucrose octasulfate and a substituted ammonium compound, wherein, when administered into the bloodstream of a mammal, said irinotecan has a half-release time from said liposomes of at least 24 hours and the irinotecan entrapped inside the liposomes is at a concentration that exceeds the irinotecan concentration in the aqueous medium;
- the method comprises at least one cycle, wherein the liposomal irinotecan is administered on day 1 of a cycle at a dose of between about 60 and about 180 mg/m², except if the patient is homozygous for the UGT1A1*28 allele, wherein the liposomal irinotecan is administered on day 1 of cycle 1 at a dose of between about 40 and about 120 mg/m², wherein the cycle is a period of 2 to 3 weeks;
- the topoisomerase I inhibitor is liposomal irinotecan administered on day 1 of a cycle at a dose of between about 90 and about 150 mg/m², except if the patient is homozygous for the UGT1A1*28 allele, wherein the liposomal irinotecan is administered on day 1 of cycle 1 at a dose of between about 60 and about 100 mg/m².
- the method comprises at least one cycle, wherein the liposomal irinotecan is administered on day 1 of a cycle at a dose of 120 mg/m², except if the patient is homozygous for the UGT1A1*28 allele, wherein the liposomal irinotecan is administered on day 1 of cycle 1 at a dose of 80 mg/m²;
- the cycle is a period of 2 weeks;
- the cycle is a period of 3 weeks;
- the method further comprises administering another therapeutic agent, the therapeutic agent is optionally chosen from a taxane, inhibitor of bcr-abl, inhibitor of EGFR, DNA damaging agent, and antimetabolite thereof, or the therapeutic agent is chosen from aminoglutethimide, amsacrine, anastrozole, asparaginase, bcg, bicalutamide, bleomycin, buserelin, busulfan, campothecin, capecitabine, carboplatin, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dichloroacetate, dienestrol, diethylstilbestrol, docetaxel, doxorubicin, epirubicin, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, letrozole, leucovorin, leuprolide, levamisole, lomustine, lonidamine, mechlorethamine, medroxyprogesterone, megestrol, melphalan, mercaptopurine, mesna, metformin, methotrexate, mitomycin, mitotane, mitoxantrone, nilutamide, nocodazole, octreotide, oxaliplatin, paclitaxel, pamidronate, pentostatin, perifosine, plicamycin, porfimer, procarbazine, raltitrexed, rituximab, sorafenib, streptozocin, sunitinib, suramin, tamoxifen, temozolomide, temsirolimus, teniposide, testosterone, thioguanine, thiotepa, titanocene dichloride, topotecan, trastuzumab, tretinoin, vinblastine, vincristine, vindesine, and vinorelbine;

the method further comprises administering non-chemical methods of cancer treatment;

the method further comprises administering radiation therapy; and/or the method further comprises administering surgery, thermoablation, focused ultrasound therapy, cryotherapy, or any combination thereof.

In some embodiments, provided is a composition comprising an effective amount of a Topoisomerase I inhibitor and an α-PD-L1 or α-PD-1 antibody, useful in human therapy. The composition can comprise an effective amount of a Topoisomerase I inhibitor and an α-PD-L1 antibody for use in treating cancer. In some embodiments, use of a composition can be for the manufacture of a medicament to treat cancer.

In some embodiments, provided is a kit for treating a cancer in a subject in need thereof, comprising: a Topoisomerase I inhibitor and an α-PD-L1 antibody; and written instructions for administering to the subject an effective amount of a Topoisomerase I inhibitor and an α-PD-L1 antibody to treat the cancer.

In some embodiments, provided is a method of treating cancer comprises administering to a patient in need thereof a therapeutically effective amount of a MM398 irinotecan liposome in combination with the administration of a therapeutically effective amount of a PD-L1 blocking antibody. The MM398 irinotecan liposome can be administered in a dose providing an amount of irinotecan equivalent to 60-120 mg/m$^2$ of irinotecan hydrochloride trihydrate. The MM-398 irinotecan liposome can be administered in a dose providing an amount of irinotecan equivalent to 60 mg/m$^2$ of irinotecan hydrochloride trihydrate. The MM-398 irinotecan liposome can be administered in a dose providing an amount of irinotecan equivalent to 80 mg/m$^2$ of irinotecan hydrochloride trihydrate. The MM-398 irinotecan liposome can be administered in a dose providing an amount of irinotecan equivalent to 120 mg/m$^2$ of irinotecan hydrochloride trihydrate. The MM-398 liposome can be administered as an infusion over 90 minutes. The administration of the MM-398 irinotecan liposome can be followed by the additional administration of leucovorin and 5-fluorouracil. The leucovorin can be administered as 200 mg/m$^2$ of the (1) form of leucovorin. The leucovorin can be administered as 400 mg/m$^2$ of the (1+d) racemic form of leucovorin. The 5-fluorouracil can be administered as a dose of 1,800-2,400 mg/m$^2$. The MM-398 can be administered at a dose of 60 mg/m$^2$ and the 5-fluorouracil is administered as a dose of 1,800 mg/m$^2$. The MM-398 can be administered at a dose of 80 mg/m$^2$ and the 5-fluorouracil is administered as a dose of 2,400 mg/m$^2$. The therapeutically effective amount of a PD-L1 blocking antibody can be administered after the MM-398. The PD-L1 blocking antibody can be nivolumab. The PD-L1 blocking antibody can be administered at a dose of 3 mg/kg. The PD-L1 blocking antibody can be administered by infusion over 60 minutes. The PD-L1 blocking antibody can be administered every 2 weeks. The MM-398 irinotecan liposome can be administered following the administration of a therapeutically effective amount of a PD-L1 blocking antibody. The cancer can be melanoma. The cancer can be metastatic melanoma. The patient can be previously been treated with nivolumab prior to the administration of the MM-398 irinotecan liposome.

EXAMPLES

Example 1: High Throughput Cytotoxicity Assay

In one embodiment, a screening approach is disclosed for assaying T-cell mediated cytotoxicity. Human melanoma cancer cell lines (BRAF/NRAS/CKIT/NF1 wild type) were incubated with 1 micromolar concentration of various test compounds for 24 hours. The human melanoma cells were stained with the cell tracker dye DDAO (APC channel) and either: (i) seeded for 24 h in 96 well plates with 1 uM of each of the 850 compounds in our screen or DMSO as a control, (ii) seeded for 24 h and then incubated with autologous T cells for 3 h, or (iii) seeded for 24 h with 1 uM compound, washed and then incubated with autologous T cells for 3 h. Cells were then washed, fixed, permeabilized and stained with a PE-conjugated antibody for activated caspase 3. Flow cytometry was used to quantify staining as a measure of apoptosis. Cells in the indicated gate would be positive for both DDAO (APC) and activated caspase 3 (PE), and were quantified as a percentage of the total number of DDAO-positive tumor cells.

Figure 1B:
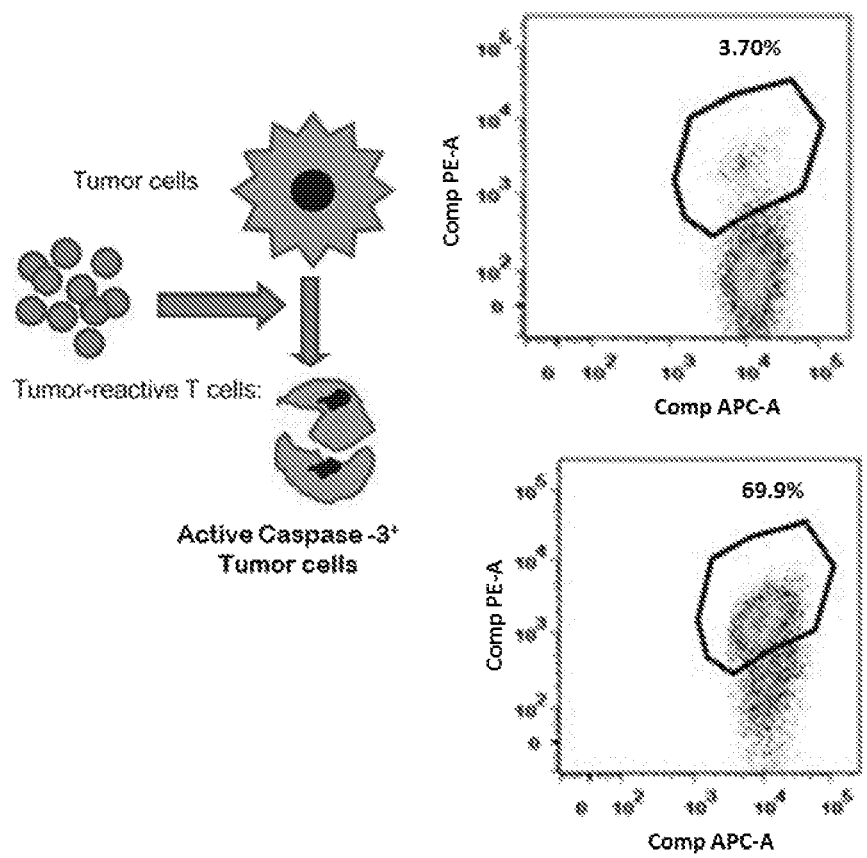

The flow cytometry analysis of intracellular staining for activated caspase 3 is shown in FIG. 1A. FIG. 1A depicts data obtained from a flow cytometry T cell cytotoxicity assay for high throughput screen. FIG. 1B depicts the methodology of the Flow cytometry based T cell cytotoxicity assay for high throughput screen. The dot plots for gating and flow cytometric analysis are depicted on the right. Briefly, patient derived melanoma tumor cells (stained with a far-red cell tracker dye), are incubated with reactive autologous T cells, followed by intracellular staining for active caspase 3. The level of cytotoxicity is measured by the percentage of active caspase 3 positive tumor cells (PE-conjugated caspase 3 antibody).

Example 2: Topoisomerase I Inhibitor Enhances T Cell Mediated Tumor Killing In Vitro in Patient Derived Melanoma Cell Lines 2338 and 2400

In another embodiment, certain topoisomerase I inhibitors are identified as enhancers of T cell mediated immunetherapy, including therapeutic combinations that can provide a synergistic improvement of CTL-mediated killing in vitro. Studies were conducted with additional patient-derived melanoma cell lines with NRAS or BRAF mutations, which also showed enhanced T cell mediated tumor killing.

Building on the observation from the high throughput assay where Top1 inhibitors were identified as hits, we further assessed the effect of Top1 inhibitors on T cell mediated killing of a number of melanoma patient-derived cell lines in vitro. In the experiments shown here, melanoma patient-derived cell lines 2338 and 2400, were treated with SN38, the active metabolite of the Top1 inhibitor irinotecan, for 24 h at a concentration of 1 uM. DMSO was used as a solvent control. Drug-treated cells were then processed as outlined in the cytotoxicity assay. Briefly, SN38-treated cells were then processed for flow cytometry analysis, or incubated with 2338 or 2400 autologous TILs for 3 h at an effector to target cell ratio (E:T) of 4:1 for 2338 and 10:1 for 2400. Flow cytometry analysis for activated caspase 3 was used to quantify the apoptotic effect of Top1 inhibitor or TIL alone, as well as the combination of Top1 inhibitor and TIL. The normalized isobolograms shown depict the CI for the combined effect of SN38 and TIL on apoptosis in melanoma tumor cells. CalcuSyn was used to compute the combination indices (CI) for the effect of SN38 and TIL. CI less than 1 indicate synergy between the 2 agents. CI greater than 1 would indicate antagonism, while CI equal to 1 indicate an additive effect. (Note: the data shown here is a subset of the data shown in FIGS. 2A, 2B and 3A of the patent application draft which shows the full experiment conducted with a concentration range of SN38 from 0.125-1 uM, and E:T ratios of 1-4:1 (2338) and 1-10:1 (2400).

FIGS. 2A, 2B, 9A, 9B, 3A and 3B depict the synergistic effect of Top 1 inhibitors (TILs) on T-cell mediated killing of melanoma cells from patient derived melanoma cell lines 2338 (FIG. 2A, top) and 2400 (FIG. 2B, bottom) by treatment with treated with autologous TILs at varying effector T cell to tumor cell (E:T) ratios for 3 hours, as measured by percent activated caspase 3. In each of FIG. 2A or 9A and 2B or 9B, cells in the leftmost group of three bars was not treated with a TIL. In each of the rightmost four groups of three bars, cells were treated at the given concentrations of TIL and no effector T-cells (right), effector T cells in a 2:1 ration with tumor cells, or effector T cells in a 4:1 ratio with tumor cells. The patient derived melanoma cell lines 2338 (NRAS Q61R) and 2400 (BRAF V600E) were treated with autologous TILs at varying effector T cell to tumor cell (E:T) ratios for 3 hours. Cells were then stained for activated caspase 3, to quantify apoptosis by flow cytometry. The 2338 and 2400 cells were treated with the Top1 inhibitor SN38 for 24 hours using a concentration range of 0.125 to 1.0 micromolar. Cells were then stained for activated caspase 3, or drug treated cells were washed and then incubated with autologous TILs for 3 hours. Apoptosis was then quantified as described.

Although we observed a good treatment effect with the combination of SN38 and anti-PD-L1, we wanted to find a Top1 inhibitor with more favorable chemical properties (e.g.: stability, solubility, ease of use of in vivo studies), to use in combination with anti-PD-L1. We therefore tested the anti-tumor activity of MM-398, a nano-liposomal formulation of irinotecan (nal-IRI), and compared it to the anti-tumor activity of Free Irinotecan to determine if this would be a suitable Top1 inhibitor to be used for further pre-clinical testing in our model system. C57BL/6 mice were inoculated with 500K mc38/gp100 tumor cells. 3 days later when tumors were palpable, mice were randomized into 1 of 5 experimental groups: (i) PBS-200 ul ip once a week, (ii) Free Irinotecan-50 mg/kg ip once a week, or MM-398 at (iii) 10 mg/kg, (iv) 20 mg/kg, or (v) 40 mg/kg iv once a week for 4 doses. From this experiment, we chose to proceed with using an MM-398 dose of 20 or 40 mg/kg for in vivo assessment in combination studies.

Using the software program CalcuSyn, we determined that Topoisomerase I (Top1) inhibition synergistically improves ability of T cells to kill tumor cells. The data shown in FIG. 3 were analyzed in CalcuSyn to compute the Combination Index (CI) of combining SN38 with 2338 and 2400 TILs. The CI are represented in the normalized isobologram above. CalcuSyn is based on the Chou-Talalay method of quantifying synergy where synergism is CI<1 (points below the line), additive effect is CI=1 (points on the line), and antagonism is CI>1 (points above the line). FIG. 3 depicts the combination Index of the Top1 inhibitor SN38 and T cell cytotoxicity. The data shown in FIG. 2 were analyzed in Calcusyn to compute the Combination index (CI) of combining SN38 with 2338 and 2400 TILs. The CI are represented in the normalized isobologram above. Calcusyn is based on the Chou-Talalay method of quantifying synergy where synergism is CI<1 (points below the line), additive effect is CI=1 (points on the line), and antagonism is CI>1 (points above the line).

Figure 8A:
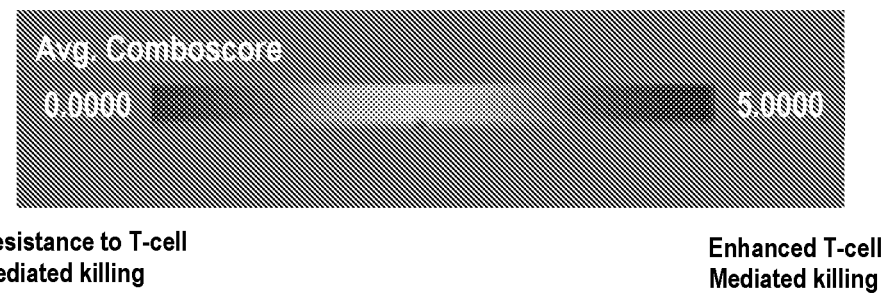
FIG. 8A shows the formula for detecting the ComboScore herein.

The level of cytotoxicity induced by the drug alone in comparison to the combination of the drug and T cells was evaluated and used to compute a comboscore to identify hits from the screen. FIG. 8A is the formula developed to calculate Comboscores, which was used as an analytical tool to initially narrow down the number of hit compounds from the HTPS.

The Tableau plot displays data obtained from the previously described high throughput cytotoxicity assay performed on the patient-derived melanoma cell line 2549, with its autologous 2549TILs (tumor infiltrating lymphocytes or T cells). The apoptosis induced by the drug alone (indicated as percentage of caspase 3 positive tumor cells on the y axis) is graphed versus the apoptosis induced by the combination of the T cells and the drug (indicated as the percentage of caspase 3 positive tumor cells on the x axis). Hits from the screen were identified based on the computed comboscore, which takes into account the level of killing induced by the combination of drug and T cells in comparison to the level of killing induced by either single agent. Drugs that improved T cell killing would generate a high comboscore (>1.5) and drugs that had no effect or a negative effect on T cell killing would generate a low comboscore (<1). The 3 Top1 inhibitors identified as hits from the screen are indicated as Top1 inhibitor 1, 2 and 3, and are: camptothecin, topotecan, and irinotecan, and were shown to increase T cell mediated killing of melanoma tumor cells.

Figure 8B:
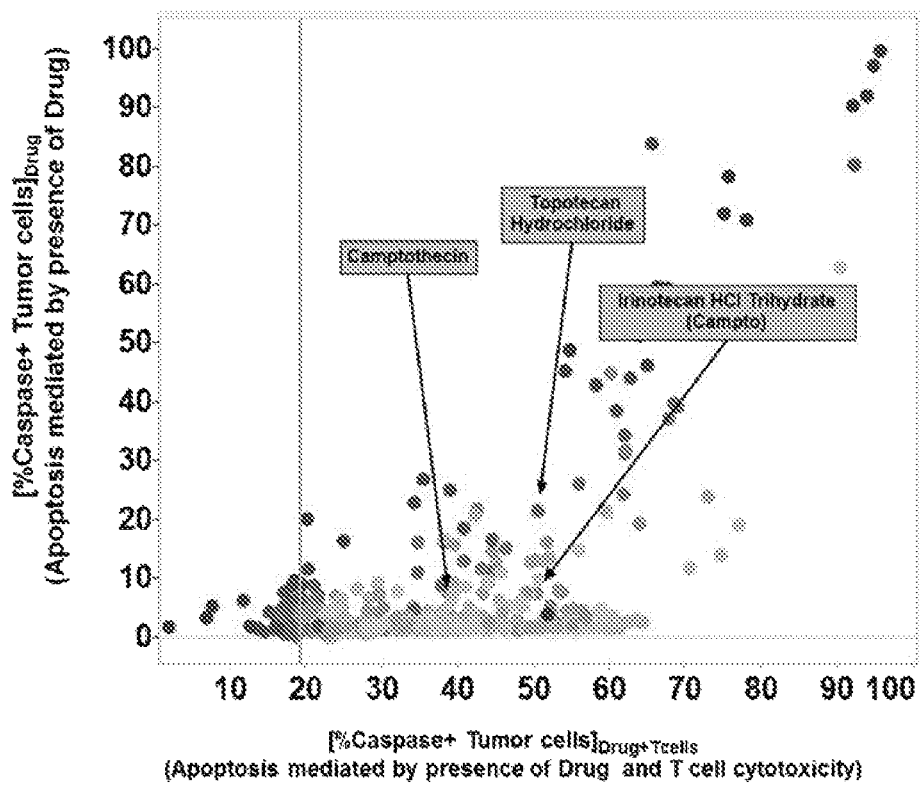
FIG. 8B is a scatter plot graph labeling selected data points for certain Top1 inhibitor compounds.
Figure 8C:
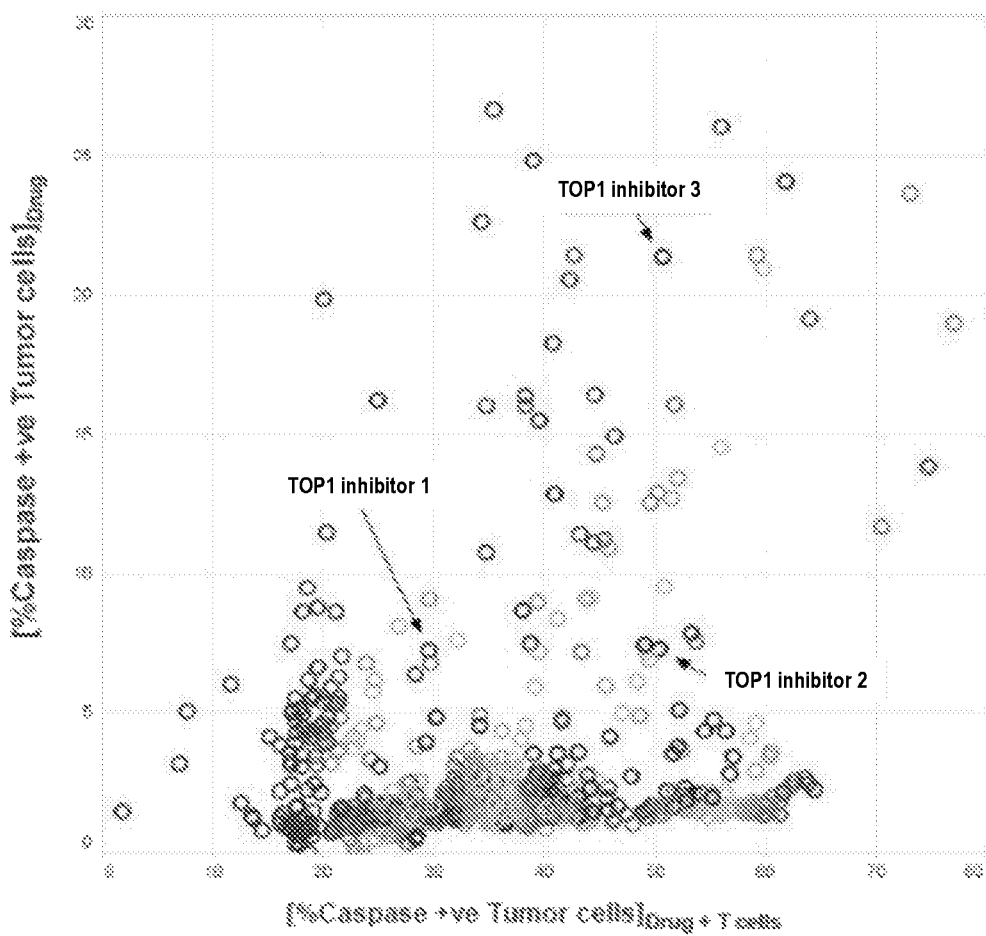
FIG. 8C is a scatter plot graph showing the % caspase positive tumor cells exposed to certain topoisomerase I inhibitor drugs plotted against % caspase positive tumor cells exposed to a certain topoisomerase I inhibitor drugs and T cells (Example 1).
Figure 9A:
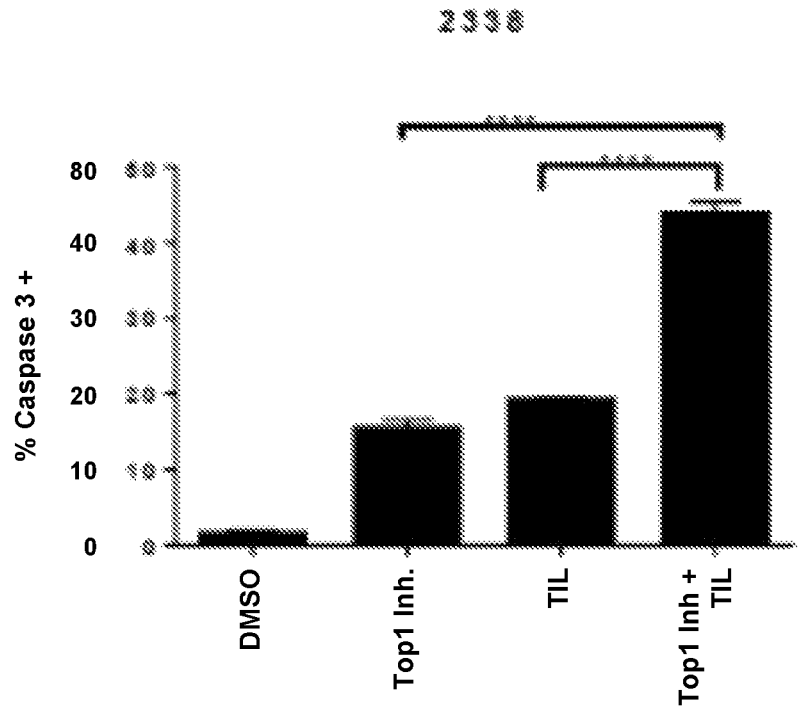
FIG. 9 shows bar graphs showing the synergistic effect of Top 1 inhibitors and autologous tumor infiltrating lymphocytes (TILs) on T-cell mediated killing of melanoma cells from patient derived melanoma cell lines 2338 (FIG. 9A) and 2400 (FIG. 9B, bottom) by treatment with treated with autologous TILs at varying effector T cell to tumor cell (E:T) ratios for 3 hours, as measured by percent activated caspase 3. In each of FIGS. 9A and 9B, cells in the leftmost group of three bars was not treated with a Top1 inhibitor or TIL, the cells measured in the second bar (from left) was treated only with the Top1 inhibitor, the cells measured in the third bar (from left) were treated with TIL and the data for the bar on the far right was obtained from a synergistic combination of TIL and the Top1 inhibitor.
Figure 9B:
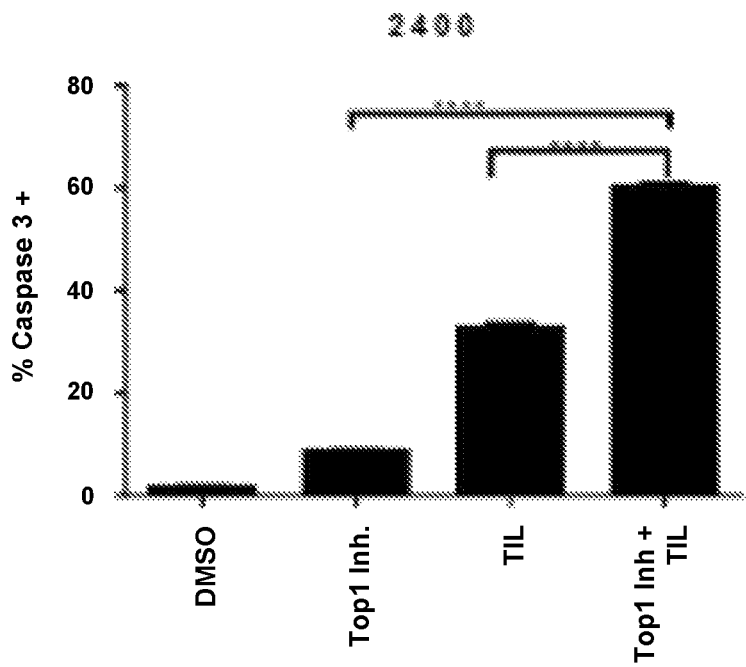

FIG. 8C is a scatter plot showing that topoisomerase I inhibitors can enhance T cell mediated killing of melanoma cancer cells. Referring to FIG. 8B, topotecan, irinotecan and camptothecin, all inhibitors of Top1 were determined to have high Comboscores, indicating that pre-treatment with these drugs caused more melanoma cells to be killed by T cells, than if they were only exposed to T cells or drug alone. Referring to the scatter plot graph of FIG. 8C, the data points show the Comboscore calculated according to the formula in FIG. 8A, ranging from low (0.5) indicating low to minimal T cell killing to high (1.5) indicating high T cell killing. The observed hits were minimally cytotoxic alone and showed synergistic T cell-mediated killing of tumor cells. Camptothecin-derived inhibitors of topoisomerase 1 were identified as top compounds from the screen.

Example 3: Combination of SN38 and Different Immune Modulatory Antibodies In Vivo In another embodiment, certain topoisomerase I inhibitors are identified as enhancers of T cell mediated immunetherapy, including therapeutic combinations that can provide a synergistic improvement of CTL-mediated killing in vitro. A series of animal model xenograft tests were performed to demonstrate the anti-tumor activity of combinations of Top1 inhibitors and a variety of immune modulatory antibodies.

Figure 10:
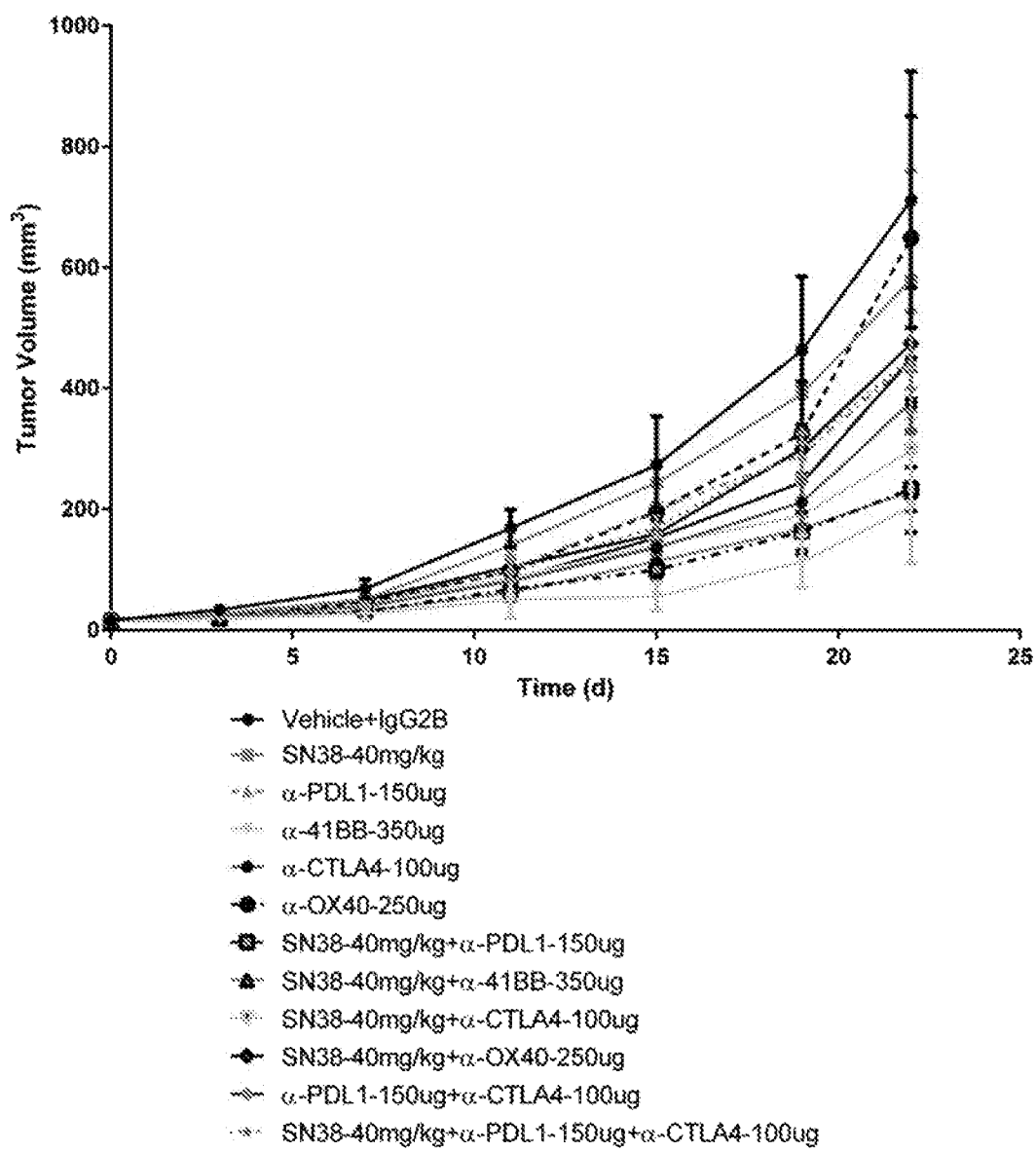
FIG. 10 is a graph of tumor volume over time in a xenograft cancer model after administration of various immune modulatory compounds with the Top1 inhibitor SN38. SN38 is the metabolite of irinotecan.
Figure 11A:
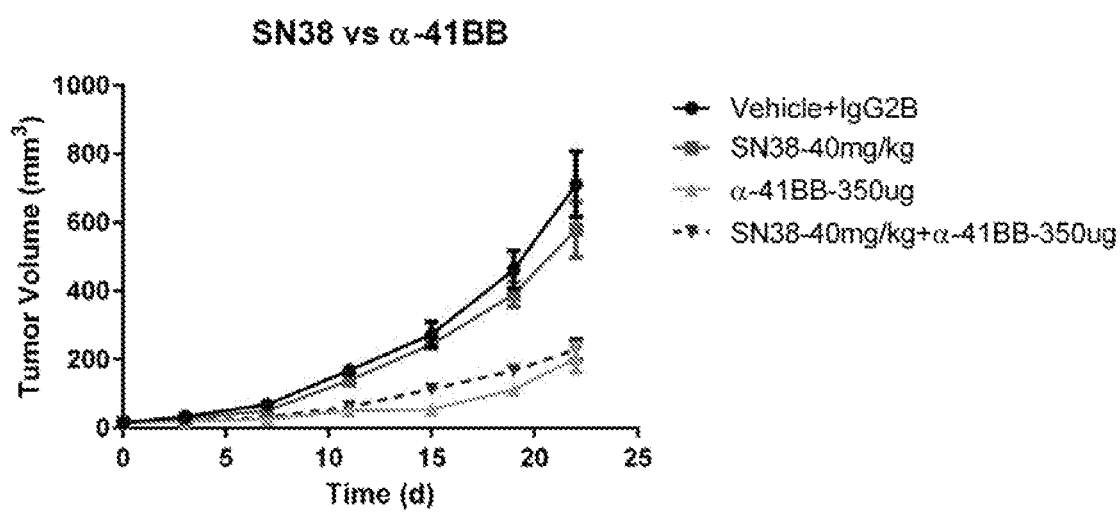
FIG. 11 are line graphs from cancer xenograft models obtained after administration of SN38 and/or anti-41BB (FIG. 11A), SN38 and/or anti-CTLA4 (FIG. 11B), SN38 and/or anti-Ox40 (FIG. 11C), and SN38 and/or anti PD-L1 and anti CTLA4 antibodies (FIG. 11D).
Figure 11B:
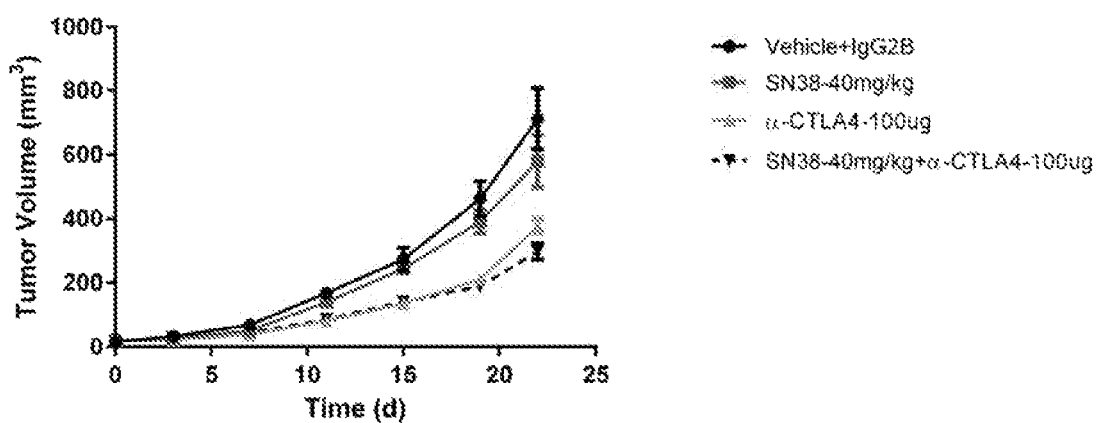
Figure 11C:
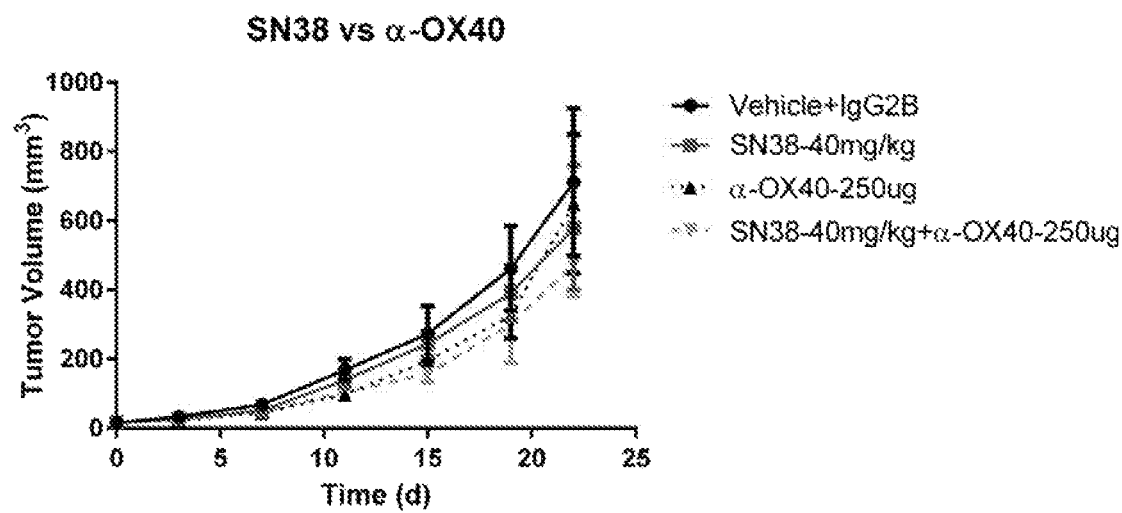
Figure 11D:
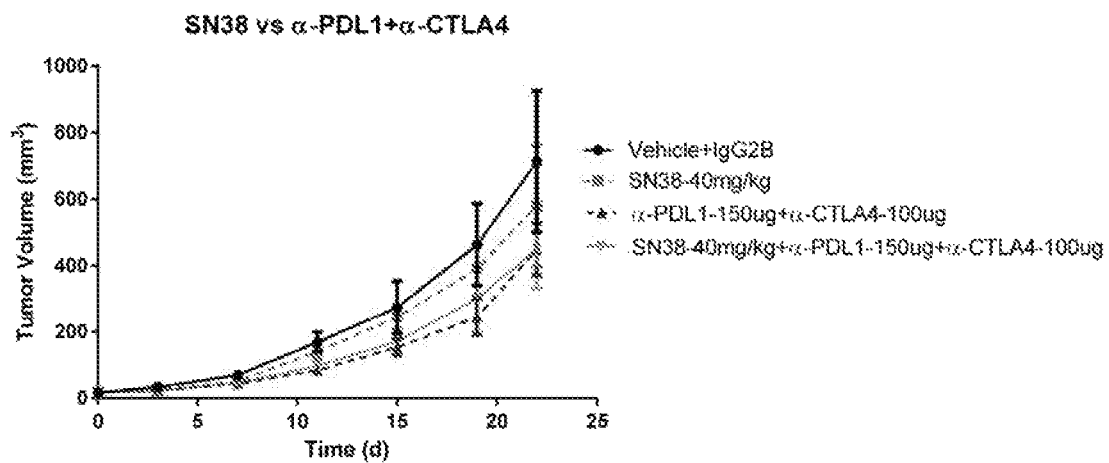

Having demonstrated in vitro that SN38 could enhance T cell mediated killing of tumor cells, we next investigated the effect of SN38 on the anti-tumor response to different T cell based immunotherapies using a pre-clinical mouse model. In this experiment, C57BL/6 mice were inoculated with 500K mc38/gp100 cells sub-cutaneously. 3 days after tumor inoculation, mice were randomized and treated with: (i) vehicle+isotype-matched control antibody (IgG 2B-clone LTF-2), (ii) SN38-40 mg/kg ip 3 times per week, (iii) anti-PD-L1-150 ug ip every 3 days (clone 10F.9G2), (iv) anti-41BB-350 ug every 3 days (clone LOB12.3), (v) anti-CTLA4-100 ug every 3 days (clone 9H10), (vi) anti-OX40-250 ug every 3 days (clone OX-86), combination of SN38 and (vii) anti-PD-L1, (viii) anti-41BB, (ix) anti-CTLA4, (x)

anti-OX40, (xi) anti-PD-L1 and -CTLA4, or a combination of (xii) anti-PD-L1 and anti-CTLA4. The data shows tumor volume over time. FIG. 10 is a graph showing the tumor volume measured over about three weeks, after treatment with the Top1 inhibitor SN38, an anti-anti PD-L1 antibody, an anti-alpho-CTLA4 antibody, anti-anti ox40 antibody, an anti-41BB antibody, and various combinations thereof.

The sequences of the antibodies are provided in the Table 2 below.

TABLE 2

| Antibody | Antibody Sequence (literature reference) |
|---|---|
| α-PD-L1 | 10F.9G2, Bioxcell |
| α -41BB | LOB12.3, Bioxcell |
| α -CTLA4 | 9H10, Bioxcell |
| α -OX40 | OX-86, Bioxcell |

FIGS. 11A-11D are graphs of measured tumor volume over time after administration of certain combinations of the Top1 inhibitor SN38 and various antibodies against anti-41BB, anti-CTLA4, anti-OX40 and anti-PD-L1 (as described in the Table 2 of Example 3 herein). The data represented in FIGS. 11A-11D were pulled out of the experiment described on FIG. 10, to show the tumor volume over time of the different combination groups in comparison to the single agent and control-treated groups. As shown, no increase in tumor control was observed in tumor-bearing mice treated with a combination of SN38 and anti-41BB, or anti-CTLA4, or anti-OX40, in comparison to tumor-bearing mice treated with SN38 alone or the mentioned immunotherapy alone.

Having demonstrated in vitro that SN38 could enhance T cell mediated killing of tumor cells, we next investigated the effect of SN38 on the anti-tumor response to different T cell based immunotherapy using a pre-clinical mouse model. In this experiment, C57BL/6 mice were inoculated with 500K mc38/gp100 cells sub-cutaneously. 7 days after tumor inoculation, mice were randomized and treated with: (i) vehicle+isotype-matched control antibody (IgG 2B-clone LTF-2), (ii) SN38-40 mg/kg ip 3 times per week, (iii) anti-PD-L1-150 ug (clone 10F.9G2), or (iv) combination of SN38 and anti-PD-L1. The data shows tumor volume over time. From this experiment, we saw no overall significance in the difference in tumor control between the different treatment groups, suggesting that further optimizations were required. Mc38/gp100 is an aggressive tumor model, which grows rapidly and is prone to ulceration. We determined that randomization and treatment can be performed 3 days after tumor inoculation instead of the delayed time point of 7 days after inoculation. Therefore, for proceeding in vivo experiments where tumor volume and survival are monitored, randomization and treatment are started 3 days after tumor inoculation when tumors are first palpable. This allows us to have a therapeutic window in which to work and determine the anti-tumor effect of the each agent singly or in combination. FIG. 4A is a graph of the measured tumor volume over time after administration of certain combinations of the Top1 inhibitor SN38 and the anti-PD-L1 antibody described in the Table 2 in Example 3 herein.

Increased tumor control in animal xenograft models was observed when liposomal irinotecan was administered in combination with certain immune modulatory antibodies. FIG. 4B is a graph of the measured tumor volume over time after administration of various concentrations of liposomal irinotecan (MM-398).

Figure 5B:
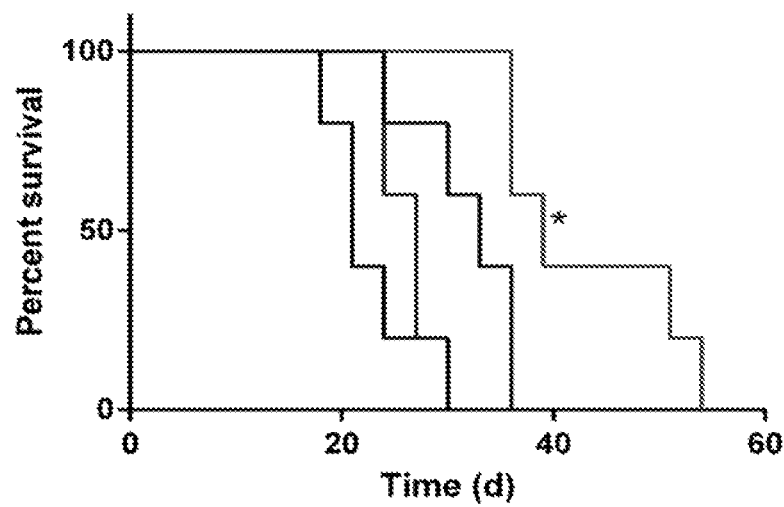
FIG. 5B is the corresponding plot of the survival curve (FIG. 5B).
Figure 5C:
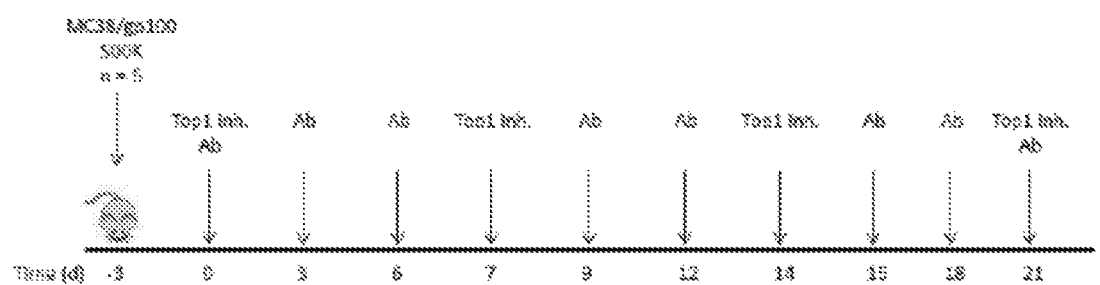
FIG. 5C is a schematic of the experiment, designed to determine the anti-tumor effect of combining MM-398 and anti-PD-L1 in our pre-clinical mouse model.

FIG. 5C is a schematic of the mouse xenograft experiment performed to obtain the data in FIGS. 5A and 5B. C57BL/6 mice were inoculated with 500K mc38/gp100 tumor cells. Three days later, tumor-bearing mice were randomized into 1 of 4 experimental groups: (i) vehicle, (ii) MM-398 (Top1 Inh.)-40 mg/kg iv once a week, (iii) anti-PD-L1-150 ug ip every 3 days, (iv) MM-398 and anti-PD-L1 (Top1 Inh+anti-PD-L1). The top panel depicts the treatment schedule. Shown below that are tumor volume over time, and a Kaplan-Meier curve for survival. The data shows that the combination of MM-398 and anti-PD-L1 produced increased anti-tumor activity over MM-398 or anti-PD-L1 alone. This also translated into significantly increased survival of tumor-bearing mice treated with the combination of MM-398 and anti-PD-L1 in comparison to cohorts treated with either single agent. Data from the experiment in FIG. 5 demonstrates that in vivo anti-tumor response and survival are increased when nanoliposomal irinotecan (nal-IRI, MM-398) is combined with α-PD-L1 antibody, including a plot of tumor volume over time in a mouse xenograft model (FIG. 5A) and a survival curve (FIG. 5B). The data was obtained from the experiment described in the schematic of FIG. 5C.

FIG. 5A is a graph of measured tumor volume over time after administration of MM-398 liposomal irinotecan and the anti-PD-L1 antibody described in the Table 2 of Example 3. FIG. 5 demonstrates that in vivo anti-tumor response and survival are increased when nanoliposomal irinotecan (nal-IRI, MM-398) is combined with α-PD-L1 antibody. FIG. 5A shows tumor volume up to day 21 (* indicates P<0.0001). C57BL/6 mice were injected s.c. with $5 \times 10^5$ MC38/gp100 cells. Three days later, when tumors were palpable, mice were randomized into treatment groups (n=5) receiving the Top1 inhibitor MM-398 irinotecan liposome (40 mg/kg), anti-PD-L1 antibody (150 micrograms/mouse), or both MM-398 irinotecan liposome and the anti-PD-L1 antibody. Vehicle control group received PBS and isotype-matched control antibody Rat IgG2b (150 micrograms). Beginning on day 3, mice received once weekly doses of MM-398 irinotecan liposome and antibody was administered every 3 days. Shown here is tumor volume up to day 21, with P<0.0001. FIG. 5A shows in vivo anti-tumor response and FIG. 5B shows survival, both increased when a MM-398 liposomal irinotecan Top1 inhibitor is combined with an anti-PDL-1 antibody. FIG. 5B shows the percent survival over time of mice treated as in FIG. 5A; the rightmost stepwise curve in 5B represents the combination of MM-398 with α-PD-L1; moving to the left, the stepwise curves represent MM-398, α-PD-L1, and vehicle, respectively (* indicates P<0.0174). The tumor survival data for mice treated with MM-398 liposomal irinotecan or anti-PD-L1 antibody alone, or in combination, is shown in FIG. 5B, having P<0.0174.

The data in FIG. 18 was obtained from an experiment designed to determine the anti-tumor effect of combining MM-398 and anti-PD1 in our pre-clinical mouse model. PD1 is the receptor for PD-L1 and forms the second part of this T cell checkpoint barrier that we can interrogate therapeutically. Therefore we wanted to see if we could see a similar increase in the anti-tumor effect with the combination of MM-398 and anti-PD1 as we observed with the combination of MM-398 and anti-PD-L1. C57BL/6 mice were inoculated with 500K mc38/gp100 tumor cells. Three days later, tumor-bearing mice were randomized into 1 of 4 experimental groups: (i) vehicle, (ii) MM-398 (Top1 Inh.)-20 mg/kg iv once a week, (iii) anti-PD1-200 ug (clone 29F.1A12) ip every 3 days, (iv) MM-398 and anti-PD1

(Top1 Inh+anti-PD-L1). The top panel depicts the treatment schedule. Shown below that are tumor volume over time, and a Kaplan-Meier curve for survival. The data shows that the combination of MM-398 and anti-PD1 produced increased anti-tumor activity over MM-398 or anti-PD1 alone. The added survival benefit of the combination of MM-398 and anti-PD1 was not as extensive as the added survival benefit observed in the combination of MM-398 and anti-PD-L1.

Figure 18A:
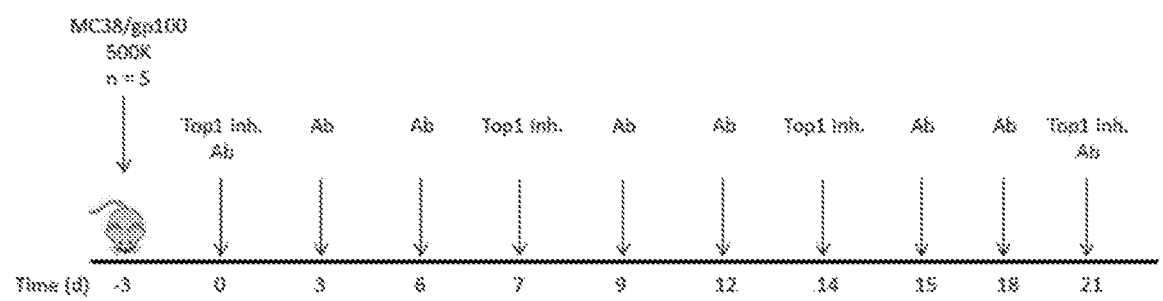
FIG. 18 demonstrates that in vivo anti-tumor response and survival are increased when nanoliposomal irinotecan (nal-IRI, MM-398) is combined with α-PD1 antibody, including a plot of tumor volume over time in a mouse xenograft model (FIG. 18B) and a survival curve (FIG. 18C). The data was obtained from the experiment described in the schematic of FIG. 18A.
Figure 18B:
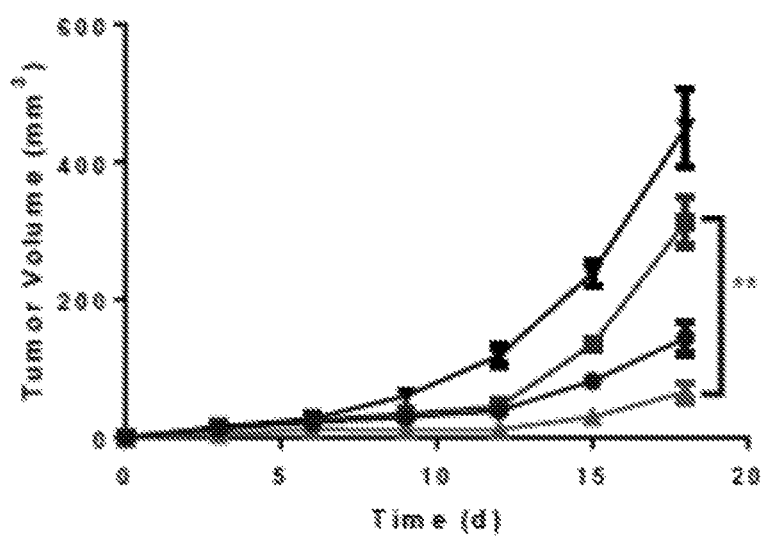
Figure 18C:
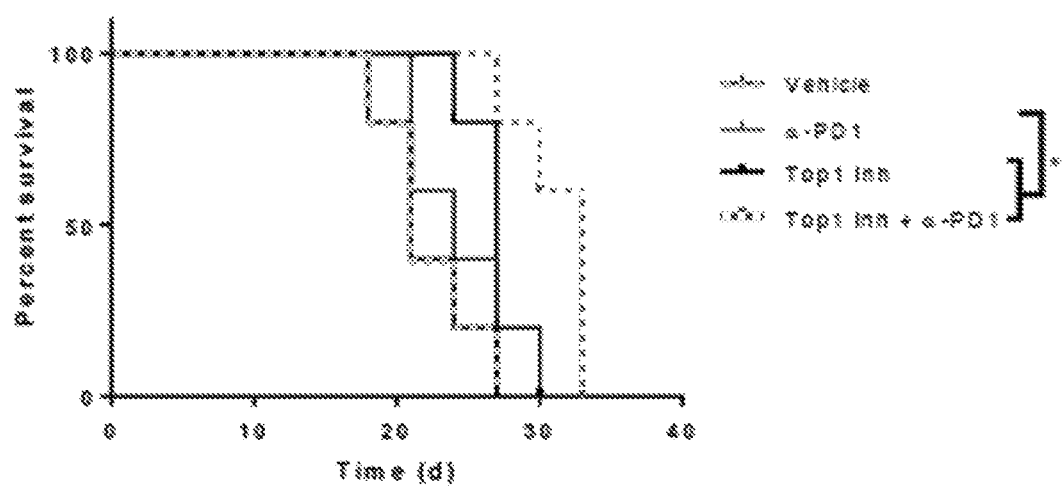

Data in FIG. 18 demonstrates that in vivo anti-tumor response and survival are increased when nanoliposomal irinotecan (nal-IRI, MM-398) is combined with α-PD1 antibody. FIG. 18A is a schematic of the mouse xenograft experiment performed to obtain the data in FIGS. 18B and 18C. FIG. 18B is a graph of measured tumor volume over time after administration of MM-398 liposomal irinotecan and the anti-PD1 antibody described in the Table 2 of Example 3. FIG. 18B shows tumor volume up to day 21 (** indicates P<0.01). C57BL/6 mice were injected s.c. with $5\times10^5$ MC38/gp100 cells. Three days later, when tumors were palpable, mice were randomized into treatment groups (n=5) receiving the Top1 inhibitor MM-398 irinotecan liposome (20 mg/kg), anti-PD1 antibody (200 micrograms/mouse), or both MM-398 irinotecan liposome and the anti-PD1 antibody. Vehicle control group received PBS and isotype-matched control antibody Rat IgG2b (200 micrograms). Beginning on day 3, mice received once weekly doses of MM-398 irinotecan liposome and antibody was administered every 3 days. Shown here is tumor volume up to day 21, with P<0.01. FIG. 18B shows in vivo anti-tumor response and FIG. 18C shows survival, both increased when a MM-398 liposomal irinotecan Top1 inhibitor is combined with an anti-PD-1 antibody. FIG. 18B shows the percent survival over time of mice treated as in FIG. 18A; the bottom curve in 18B represents the combination of MM-398 with α-PD1; moving upward, the stepwise curves represent MM-398, α-PD1, and vehicle, respectively (* indicates P<0.0273). The tumor survival data for mice treated with MM-398 liposomal irinotecan or anti-PD1 antibody alone, or in combination, is shown in FIG. 18C, having P<0.0273.

Example 4: Profile of Immune Response to Administration of Liposomal Irinotecan in Combination with Anti-PD-L1 Antibody In another embodiment, certain topoisomerase I inhibitors are identified as enhancers of T cell mediated immunetherapy, including enhanced anti-tumor response using a combination of liposomal irinotecan (e.g., MM-398) and anti-PD-L1 antibody in vivo.

Figure 12:
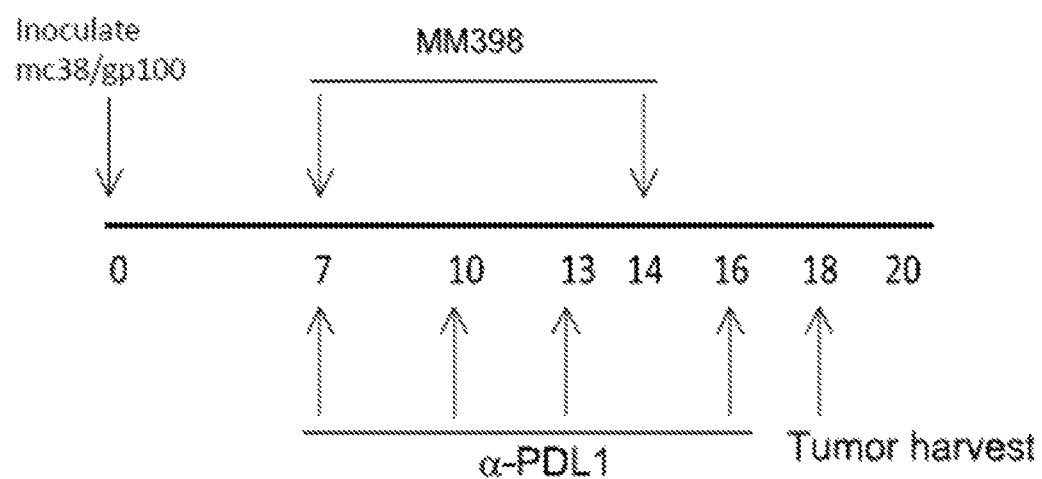
FIG. 12 is a schematic of an animal model experiment to determine the effect of MM-398 liposomal irinotecan and an anti-PD-L1 antibody on different immune cell populations.

FIG. 12 is a schematic of a mouse xenograft experiment including the administration of MC38 colon cancer cell which have been transduced to express the melanoma antigen gp100, followed by administration of liposomal irinotecan and an anti-PD-L1 antibody. The diagram in FIG. 12 outlines our experimental design for exploring the effect of MM-398 or anti-PD-L1 alone or in combination on different immune cell subsets in the tumor microenvironment. C57BL/6 mice were inoculated with 500K mc38/gp100 tumor cells. 7 days later, mice were randomized into 1 of 4 experimental groups: (i) vehicle, (ii) MM-398-40 mg/kg iv once a week, (iii) anti-PD-L1-150 ug ip every 3 days, (iv) MM-398 and anti-PD-L1. Tumors were harvested on day 18 (post tumor inoculation), and subjected to flow cytometry analysis for: CD8 T cells and their effector function, regulatory T cells, and myeloid derived macrophages.

Figure 13A:
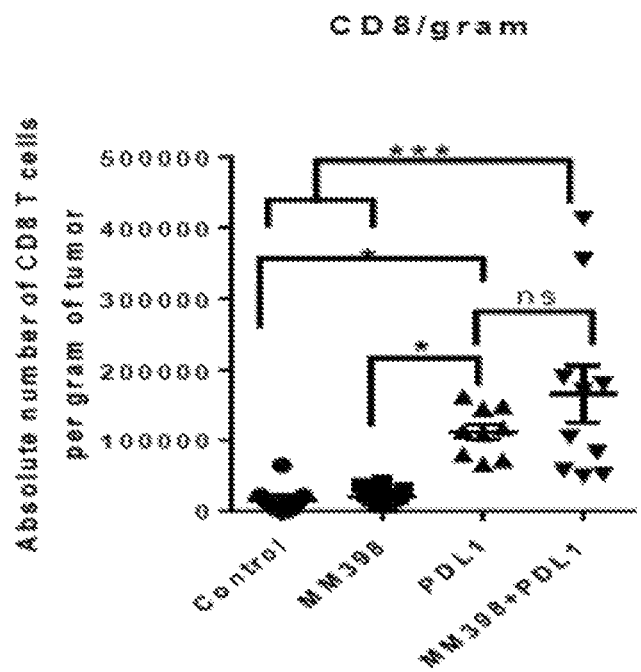
FIG. 13 are graphs showing measurements taken from the animal model test of FIG. 12, including CD8/gram (FIG. 13A), CD8/Treg (FIG. 13B), GranzA/gram (FIG. 13C), GranzB/gram (FIG. 13D) and Mac/gram (FIG. 13E).
Figure 13B:
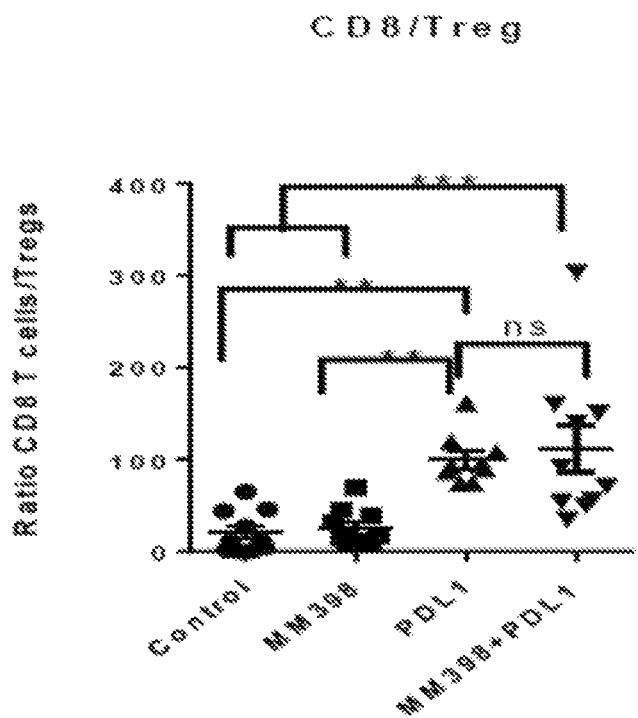

Tumors from the experiment described in FIG. 12 were dissociated and analyzed by flow cytometry analysis for effector and regulatory T cells. FIGS. 13A-13B are graphs obtained from the following experiment. CD8 T cells were identified based on the following criteria: CD3+, CD8+. Regulatory T cells are defined as CD3+, CD4+, CD25+, and FoxP3+. We observed that while the MM-398 alone group exhibited no increase in the CD8 T cell population, both the anti-PD-L1 alone and the combination group of MM-398 and anti-PD-L1 exhibited an increase in the number of CD8 T cells per gram of tumor in comparison to the control group. The same is true for the ratio of CD8 T cells to regulatory T cells (CD8/Treg), which is higher in the anti-PD-L1 group and the combination group. It would seem that this increase in the CD8 T cell number and the ratio of the CD8 T cells to regulatory cells is being driven more by the effect of the anti-PD-L1 antibody.

Figure 13C:
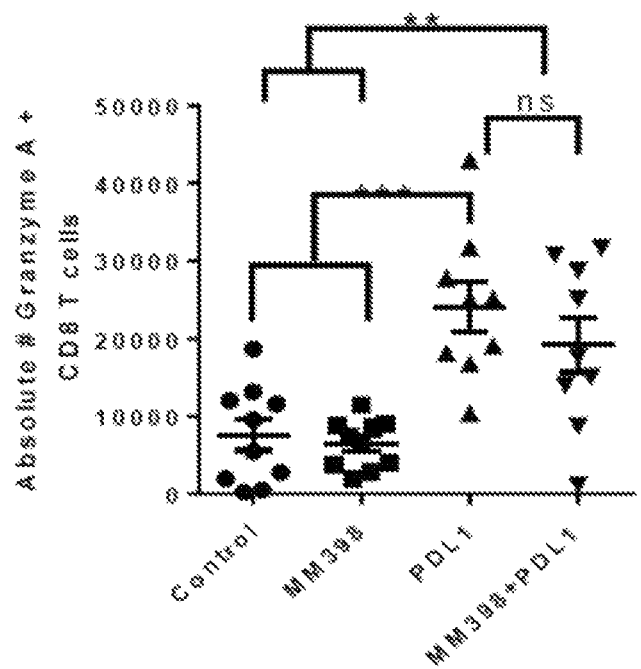
Figure 13D:
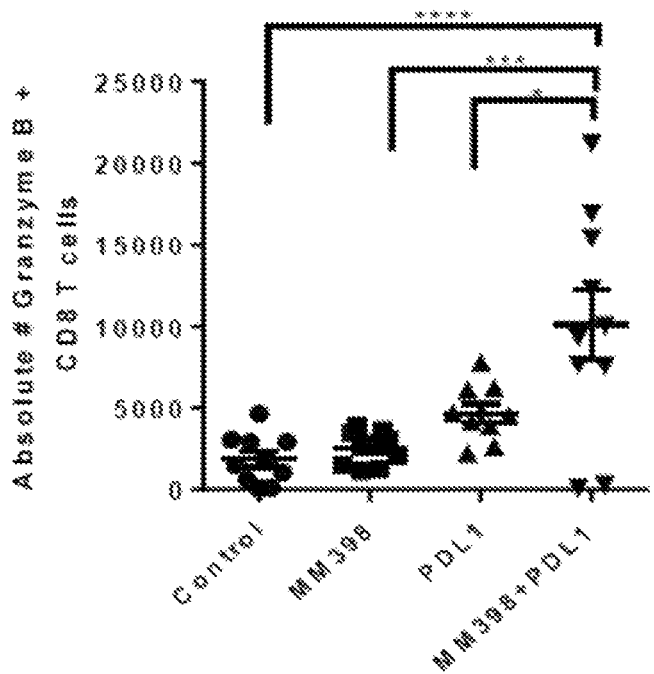

Data in FIGS. 13C and 13D was obtained as follows. The effector activity of CD8 T cells was assessed by looking at the expression levels of granzyme A and B, which are functional enzymes produced by T cells which deliver cytolytic signals to target tumor cells. Effector activity was quantified based on flow cytometry analysis of: CD3+, CD8+, and GzA/GzB+. As shown in the FIGS. 13C and 13D, there is a significant increase in the level of granzymes, particularly in granzyme B which is the predominant effector molecule for CD8 T cells. The data shows that the highest amount of cytolytic activity was detected in CD8 T cells in the setting of the combination of MM-398 and anti-PD-L1. Further experiments are required to more comprehensively understand the effect of MM-398 on the tumor and the tumor microenvironment that would be permissive for increased T cell cytolytic activity.

Figure 13E:
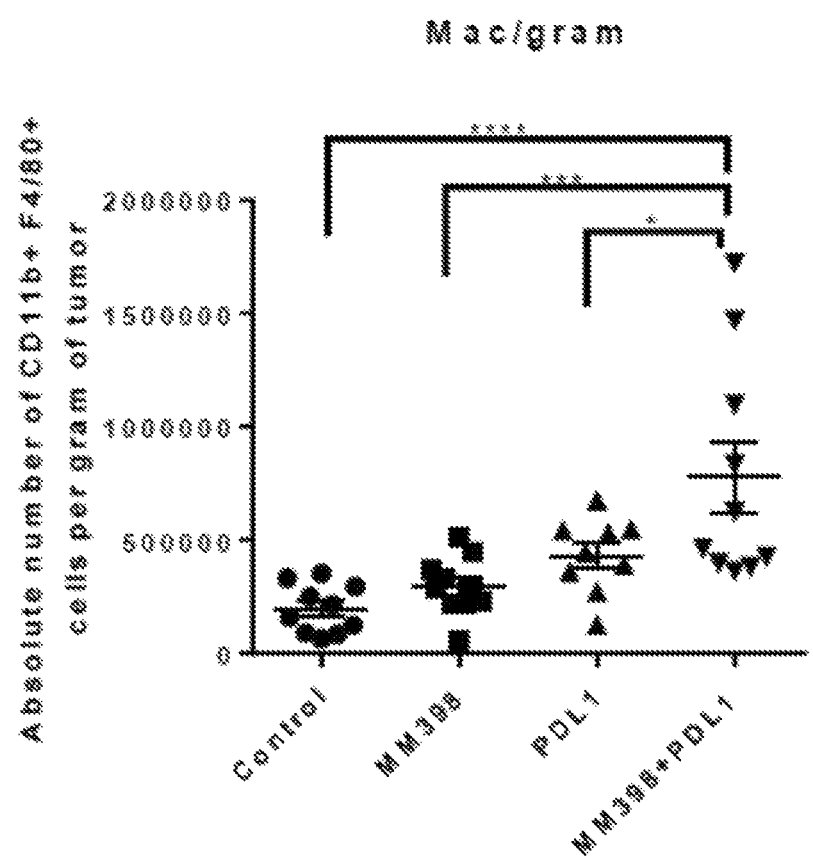

Data in FIG. 13E was obtained as follows. In addition to looking at different T cell populations, we also assessed the effect of MM-398, anti-PD-L1, and the combination of the two on the myeloid derived macrophages defined by: CD11b+, F4/80+ cells. The data in FIG. 13E shows a general trend towards an increase in the number of macrophages detected in the single agent treated groups and also in the combination treatment group, with the highest number of macrophages per gram of tumor detected in the combination setting. The formulation of MM-398 lends itself to uptake by macrophages and it was unsurprising to us to note this observation of increased tumor associated macrophages.

Example 5: Top1 Inhibition Resulting in Upregulation of Tumor Protein 53-Induced Nuclear Protein 1 (Teap)

In order to better understand the tumor molecular mechanisms involved in Top1 inhibitor-enhancement of T cell mediated killing, we performed gene expression analysis of SN38-treated melanoma cell lines (DMSO-treatment of the same melanoma cell lines served as controls). For this analysis, 4 melanoma cell lines were chosen (A: 2338, B: 2400, C: 2549, and D: 2559) and treated for 24 h with 1 uM SN38 before being harvested for microarray analysis using the Illumina HumanHT-12 v4 Expression BeadChip array. The data collected was pathway analysis performed using Ingenuity Pathway Analysis (IPA) to determine what signaling pathways and cell master regulators are differentially regulated in SN38-treated cells in comparison to DMSO-treated cells. Pathways and regulators are ranked based on the Log 2 fold change and on the activation score respectively. The data indicated a significant and highly ranked activation of the p53 signaling pathway in our Top1-inhibitor treated tumor cells.

IPA analysis of the differential activation of the p53 signaling pathway in our SN38-treated melanoma tumor cells also indicated that based on the gene expression changes of the factors involved in the p53 signaling pathway, there was a significant activation of the cell death pathway in these cells and a repression in proliferative and survival signals. These computations based on the gene expression changes are indicative of an increased apoptotic response in Top1 inhibitor-treated tumor cells. This is important for our studies which seek to understand how Top1 inhibitors can modulate tumor cells to make them more susceptible to additional death signals from T cells.

In some embodiments, the discovery of synergy between Topoisomerase I inhibition and checkpoint blockade provides novel methods of treating cancer comprising the administration of a Top1 inhibitor (e.g., liposomal irinotecan) with a checkpoint inhibitor compound. In this embodiment, the role of a p53 regulatory gene is identified as playing an essential role in the enhanced response to T cell mediated killing, including topoisomerase I inhibition resulting in upregulation of Tumor protein 53-induced nuclear protein 1 ("Teap"), Teap overexpression observed to recapitulate the relevant phenotype and the observation that knockdown of Teap impedes the relevant phenotype. Microarray analysis suggested that p53 inducible nuclear protein 1 (TP53INP1) levels increase in response to Top1 inhibition. In Example 5, the inventors investigated whether TP53INP1 (Teap) can act as an apoptotic sensor and lower the apoptotic threshold in the tumor cells through activation of a TP53 regulated apoptotic pathway, thereby making them more sensitive to T cell induced cell death, in addition to whether Top1 inhibition can increase effector T cells and increase the ratio of effector to regulatory T cells.

The p53 pathway is highly activated following the inhibition of Top1. The Top1 inhibition results in activation of the cell death pathway and repression of proliferation and survival signaling. The induction of p53 pathway can be activated by p73 in the absence of p53. Teap induces apoptosis in response to cell stress, including the regulation of stress response genes like p21, bax or md$^{m2}$. Teap can also regulate autophagy via interactions with LC3 and regulation of ATGS and beclin-1 activity.

FIG. 6B is a gene expression "heat map" for various genes expressed in three cell lines (2338, 2400 and 2549). The data shown in FIG. 6B represents a portion of the gene expression analysis which was described above. This portion of the data focuses on the differential expression of some genes related to p53 signaling. In particular, we have chosen to focus on TP53INP1 (or Teap), which is a p53 regulatory gene shown to be involved in directing an apoptotic response in tumor cells (Gironella et al., Natl Acad Sci USA 2007; Tomasini et al., J Biol Chem 2001). We observed a significant upregulation in the expression of Teap with SN38 treatment in melanoma. This phenotype was also validated by quantitative real time PCR (qRT-PCR) performed on a number of melanoma patient-derived tumor cell lines treated with 2 different Top1 inhibitors (Top1 inh. 1=SN38, Top1 inh. 2=Topotecan).

FIG. 14 is a graph showing the comparative change in TP53INP1 in response to a first Top1 inhibitor and a second Top1 inhibitor.

Figure 15A:
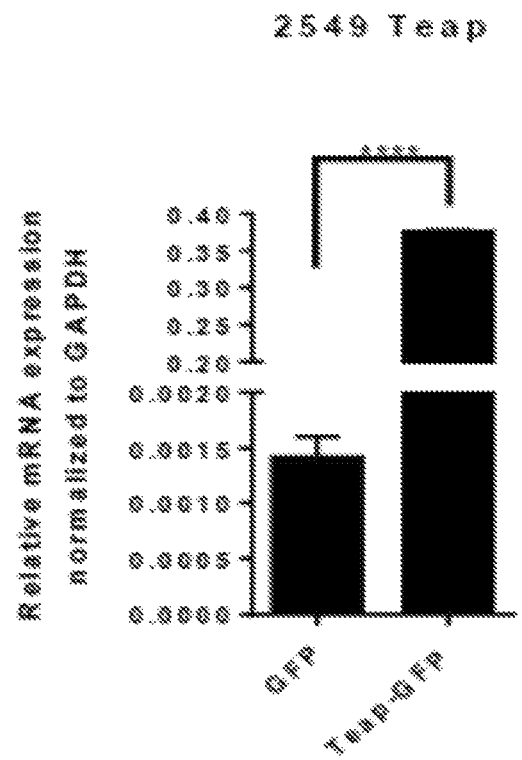
FIG. 15 is a collection of graphs showing measurements of relative mRNA expression and overexpression (FIG. 15A) and % caspase 3 positive (FIG. 15B) in 2549 Teap.
Figure 15B:
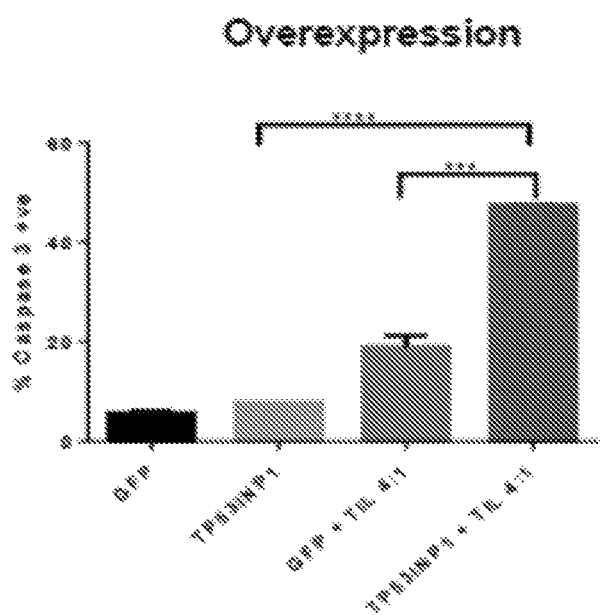

Overexpression of Teap increases T cell mediated killing in vitro. Given the significant increase observed in the expression level of TP53INP1 in Top1 inhibitor-treated tumor cells, we next investigated the functional relevance of this change to T cell mediated killing using our in vitro cytotoxicity assay. We used a lentivirus system to overexpress GFP-tagged Teap in melanoma tumor cells (overexpression of GFP was used as a control). We validated the overexpression of Teap in the tumor cells by qRT-PCR. We incubated GFP or Teap overexpressing 2549 melanoma cells with 2549 autologous T cells to determine what effect overexpression of Teap would have on T cell mediated killing of the tumor cells. We observed increased T cell killing of 2549 tumor cells overexpressing Teap in comparison to control GFP-overexpressing 2549 cells. This observation recapitulated what we observed with treatment of melanoma cells with Top1 inhibitors; which resulted in increased expression of Teap as well as increased T cell mediated killing of tumor cells. FIGS. 15A and 15B are graphs showing relative mRNA expression of Teap normalized to GAPDH (FIG. 15A) and % Caspase 3 positive (FIG. 15B).

Figure 16A:
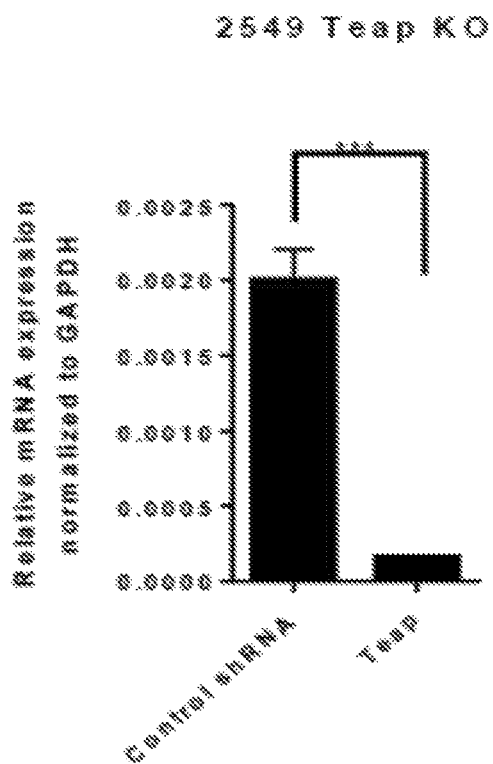
FIG. 16 is a collection of graphs showing measurements of relative mRNA expression and gene silencing (FIG. 16A) and % caspase 3 positive (FIG. 16B) in 2549 Teap KO.
Figure 16B:
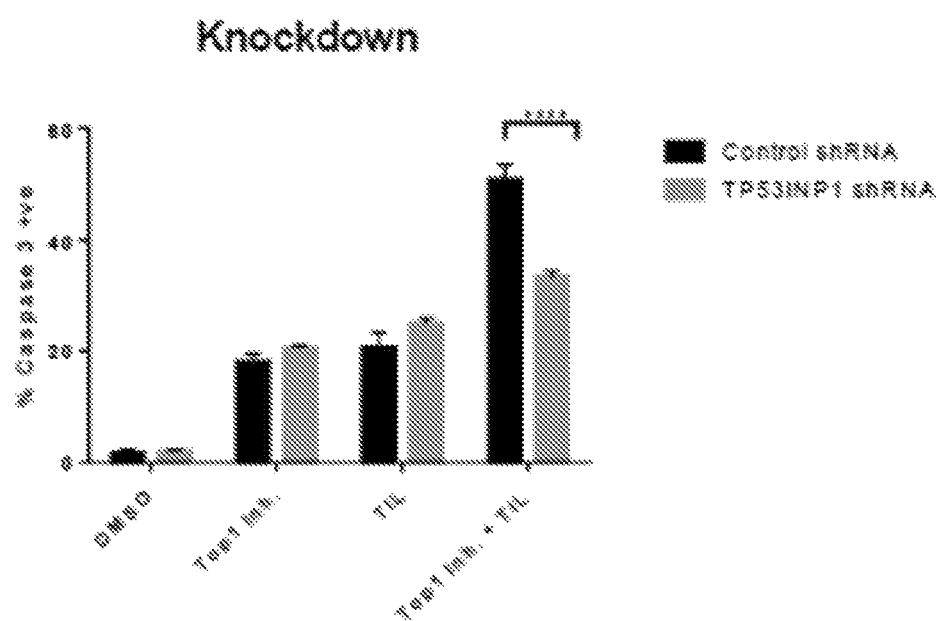

Silencing Teap impedes T cell mediated killing in Top1 inhibitor treated tumor cells. We then asked the complementary question of the necessity of Teap for Top1 inhibitor enhancement of T cell mediated killing of melanoma tumor cells. We addressed this question by using lentiviral shRNAs to silence the expression of Teap in melanoma tumor cells (shRNAs targeting luciferase were used as a control). We validated the knockdown of Teap expression by qRT-PCR. We then asked whether or not Top1 inhibitor-treatment would result in increased T cell mediated killing of melanoma tumor cells if the expression of Teap was silenced. As is shown, silencing of Teap in melanoma cells impeded the capacity of Top1 inhibitor treatment to enhance T cell mediated killing of tumor cells. However, TEAP silencing did not impede the caspase activation in tumor cells by TOP1 inhibition or TIL co-incubation alone. This indicates that Teap is necessary for the enhancement observed in T cell mediated killing of Top1 inhibitor-treated tumor cells. FIG. 16A is a graph showing relative mRNA expression normalized to GAPDH for 2549 and % Caspase 3 positive (FIG. 16B) for a Teap knockout melanoma cell line.

Example 6: Combination Top1/Immunomodulatory Therapy for the Treatment of Human Cancer In another embodiment, methods of treating humans diagnosed with cancer such as melanoma comprise administration of a topoisomerase I inhibitor (e.g., MM-398 liposomal irinotecan) in combination with an anti-PD1 antibody (e.g., nivolumab).

Figure 17A:
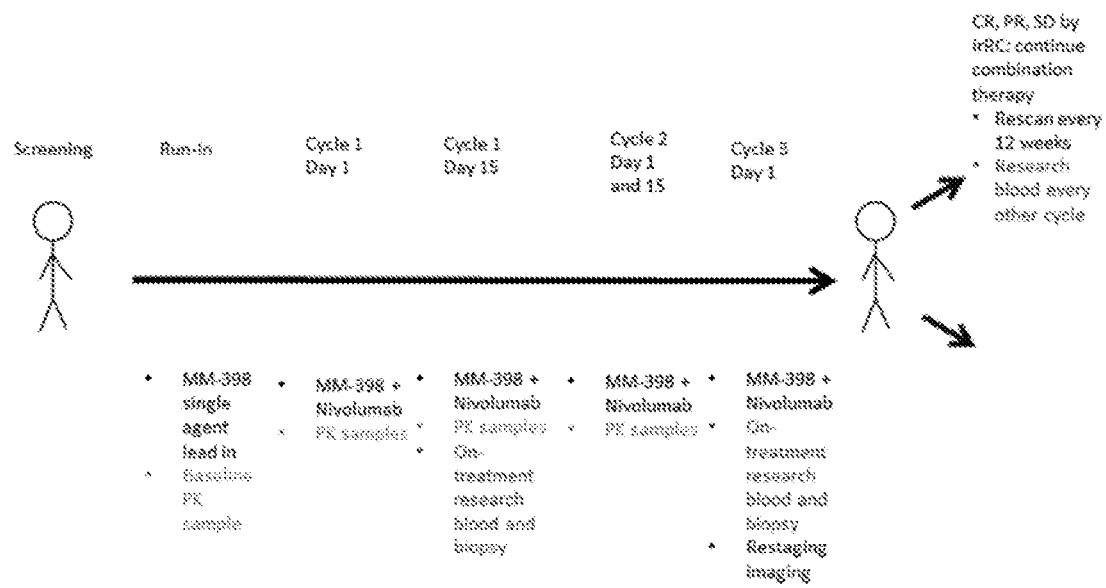
FIG. 17A is a schematic for a first method of administering a combination of MM-398 liposomal irinotecan and nivolumab to a human in need thereof.
Figure 17B:
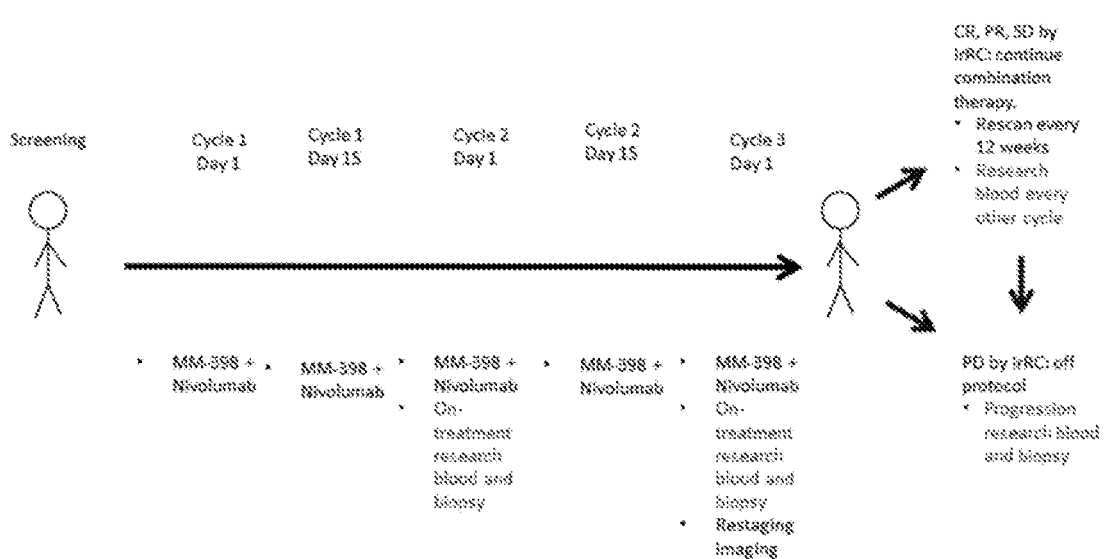
FIG. 17B is a schematic for a second method of administering a combination of MM-398 liposomal irinotecan and nivolumab to a human in need thereof.

FIGS. 17A and 17B are schematic diagrams of exemplary methods of treating a human with a combination therapy of MM-398 liposomal irinotecan and the anti-PD1 therapy nivolumab. The method of FIG. 17A is useful, for example, to determine the recommended Phase II dose of an anti-PD-1 antibody (e.g. nivolumab) and a liposomal irinotecan (e.g., MM-398) in a combination therapy, including determination of pharmacokinetics of the combination therapy. The method of FIG. 17B is useful, for example, to determine the overall response rate of an anti-PD-1 antibody (e.g. nivolumab) and a liposomal irinotecan (e.g., MM-398) in a combination therapy in a patient who is refractory to prior anti PD-1 antibody therapy, including the determination of progression free survival and overall survival, and evaluation of the safety profile of the combination therapy. One or both methods in FIGS. 17A and 17B can further include one or both of the following: (a) assessing pre and post treatment biopsy and blood samples for biomarker analysis; including assessment of immunologic and molecular markers in patients with metastatic melanoma enrolled on with combination therapy, including specifically an assessment of TP53NP1 (Teap) which has been identified as a target of interest based on pre-clinical studies, and/or (b) immunological markers to be analyzed include CD4, CD8, CD25, FoxP3 to monitor circulating effector and regulatory T cells. The expression of tumor intrinsic factors such as TP53INP1 and pro-apoptotic molecules can also be monitored during either or both methods of FIGS. 17A and 17B. The methods can be practiced in medically appropriate patients. Preferably, the patients have one, multiple or all of the following characteristics: Age >18, ECOG 0–; Measurable disease by RECIST 1.1; tumor amenable to serial biopsy that is not counted as measurable disease; adequate organ/marrow function; and/or treatment refractory to anti PD-1 or anti PD-L1 based therapy. Also preferably, patients with active autoimmune diseases with requirement for chronic steroid replacement (>10 mg prednisone/equivalents) are excluded from treatment. In addition patients with prior CNS metastases can be allowed provided that disease is treated and stable at least 4 weeks prior to treatment.

The methods of treatment include treating the human patient with at least one of dose level 1, −1, 2 or 3 from the Table 3 below given once every 14 days intravenously (in a 28-day treatment cycle), corresponding to specific doses of MM-398 liposomal irinotecan (dose based on free base of irinotecan) and nivolumab.

TABLE 3

| Dose Level | MM-398 (mg/m²) | Nivolumab (mg/kg) |
|---|---|---|
| −1 | 43 | 3 |
| 1 (starting dose) | 50 | 3 |
| 2 | 70 | 3 |
| 3 | 80 | 3 |

Preferably, the MM-398 liposomal irinotecan is administered prior to the nivolumab. Preferably, the methods of treatment are used to treat human patients diagnosed with a form of cancer that is FDA approved for nivolumab. Nivolumab is currently FDA-approved in melanoma, non-small cell lung cancer (NSCLC), Renal Cell Cancer (RCC), and Hodgkin lymphoma. A Bayesian design can be used for a phase 1 study using the method of treatment in FIG. 17A. A phase II study using the method of treatment in FIG. 17B can have a target of 20% overall response rate (ORR) (e.g., estimate a total of 50 patients treated to target of 20% ORR with one-sided significance level of 5% and power of 75%).

The protocol above could be altered in several ways to assess efficacy and proper dosing. Pembrolizumab could be used in place of nivolumab, to be tested in combination with liposomal irinotecan. Pembrolizumab is typically dosed at 2 mg/kg every 3 weeks, so the protocols shown in FIGS. 17A and 17B could be modified such that each cycle would be three weeks long instead of two. Preferably, the methods of treatment are used to treat human patients diagnosed with a form of cancer that is FDA approved for pembrolizumab. Pembrolizumab is currently FDA-approved in melanoma. Alternatively, an anti-PD-L1 antibody could be used in place of an anti-PD-1 antibody.

Other Embodiments

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

All references cited in this specification are hereby incorporated by reference. The discussion of the references herein is intended merely to summarize the assertions made by their authors and no admission is made that any reference constitutes prior art relevant to patentability. Applicant reserves the right to challenge the accuracy and pertinence of the cited references.

What is claimed is:

1. A method of treatment of cancer in a host in need thereof, comprising administering to the host a combination of liposomal irinotecan and nivolumab, in an amount and in a schedule of administration that is therapeutically synergistic in the treatment of said cancer.

2. The method according to claim 1, wherein said schedule comprises administering to a human host during a 28-day treatment cycle: a total of 50 mg/m² liposomal irinotecan (free base) followed by the administration of 3 mg/kg nivolumab, once every two weeks for two weeks; and repeating said 28-day treatment cycle until a progression or an unacceptable toxicity is observed.

3. The method according to claim 1, wherein said schedule comprises administering to a human host during a 28-day treatment cycle: a total of 43 mg/m² liposomal irinotecan (free base) followed by the administration of 3 mg/kg nivolumab, once every two weeks for two weeks; and repeating said 28-day treatment cycle until a progression or an unacceptable toxicity is observed.

4. The method according to claim 1, wherein said schedule comprises administering to a human host during a 28-day treatment cycle: a total of 70 mg/m² liposomal irinotecan (free base) followed by the administration of 3 mg/kg nivolumab, once every two weeks for two weeks; and repeating said 28-day treatment cycle until a progression or an unacceptable toxicity is observed.

5. The method according to claim 1, wherein said schedule comprises administering to a human host during a 28-day treatment cycle: a total of 80 mg/m² liposomal irinotecan (free base) followed by the administration of 3 mg/kg nivolumab, once every two weeks for two weeks; and repeating said 28-day treatment cycle until a progression or an unacceptable toxicity is observed.

6. The method according to any one of claims 1-5, wherein the cancer is selected from the group consisting of melanoma, NSCLC and RCC.

7. The method according to claim 6, wherein the cancer is melanoma.

8. The use according to claim 1, wherein the liposomal irinotecan comprises liposomes having a unilamellar lipid bilayer vesicle, approximately 110 nm in diameter, which encapsulates an aqueous space containing irinotecan in a gelated or precipitated state as the sucrose octasulfate salt; wherein the vesicle is composed of 1,2-distearoyl-sn-glycero-3-phosphocholine (DSPC) 6.81 mg/mL, cholesterol 2.22 mg/mL, and methoxy-terminated polyethylene glycol (MW 2000)-distearoylphosphatidyl ethanolamine (MPEG-2000-DSPE) 0.12 mg/mL.

9. The method according to claim 8, wherein each mL also contains 2-[4-(2-hydroxyethyl) piperazin-1-yl]ethanesulfonic acid (HEPES) as a buffer 4.05 mg/mL and sodium chloride as an isotonicity reagent 8.42 mg/mL.

10. The method according to claim 9, wherein the host is human and is known not to be homozygous for the UGT1A1*28 allele.

11. The method according to claim 1, wherein the combination of the anti-neoplastic agent liposomal irinotecan and 3 mg/kg of the anti-neoplastic agent nivolumab is administered to a human host once every two weeks for a total of at least six weeks with each administration of liposomal irinotecan comprising the administration of a total of 43, 50, 70 or 80 mg/m$^2$ liposomal irinotecan (free base) followed by the administration of 3 mg/kg nivolumab on the same day as the liposomal irinotecan, and no other anti-neoplastic agents are administered during the six weeks.

12. The method according to claim 1 wherein no other antineoplastic agent is administered for the treatment of the cancer.

* * * * *